(12) United States Patent
Nagase et al.

(10) Patent No.: US 8,965,081 B2
(45) Date of Patent: Feb. 24, 2015

(54) METHOD FOR ACQUIRING HAIR CHARACTERISTIC DATA AND APPARATUS FOR ACQUIRING THE SAME

(75) Inventors: Shinobu Nagase, Tokyo (JP); Yusuke Ezawa, Tokyo (JP); Akira Mamada, Tokyo (JP)

(73) Assignee: Kao Corporation, Tokyo (JP)

( * ) Notice: Subject to any disclaimer, the term of this patent is extended or adjusted under 35 U.S.C. 154(b) by 397 days.

(21) Appl. No.: 13/388,866

(22) PCT Filed: Jul. 23, 2010

(86) PCT No.: PCT/JP2010/004714
§ 371 (c)(1),
(2), (4) Date: Feb. 3, 2012

(87) PCT Pub. No.: WO2011/016198
PCT Pub. Date: Oct. 2, 2011

(65) Prior Publication Data
US 2012/0128220 A1 May 24, 2012

(30) Foreign Application Priority Data
Aug. 3, 2009 (JP) .................................. 2009-181066

(51) Int. Cl.
*G06K 9/00* (2006.01)
*G01N 23/04* (2006.01)
(Continued)

(52) U.S. Cl.
CPC ............. *G01N 23/04* (2013.01); *A61B 5/1072* (2013.01); *A61B 5/448* (2013.01); *G01N 21/65* (2013.01); *G01N 21/84* (2013.01); *A61B 5/0075* (2013.01); *A61B 5/0077* (2013.01); *G01N 2021/3595* (2013.01); *G01N 2021/8444* (2013.01);
(Continued)

(58) Field of Classification Search
None
See application file for complete search history.

(56) References Cited

U.S. PATENT DOCUMENTS 8,463,006 B2 * 6/2013 Prokoski ....................... 382/128
8,484,155 B2 * 7/2013 Yamaguchi et al. ............. 706/54
(Continued)

FOREIGN PATENT DOCUMENTS

| JP | 9-178738 | 7/1997 | |
| JP | 2005134344 A * | 5/2005 | ............... G01N 3/20 |
| JP | 2006-170915 | 6/2006 | |

OTHER PUBLICATIONS

Bryson, Cortical cell types and intermediate filament arrangments correlate with fiber curvature in Japanese human hair, Dec. 2008, Journal of structural Biology. 166 (2009) 46-58.*
(Continued)

*Primary Examiner* — Jayesh A Patel
*Assistant Examiner* — Iman K Kholdebarin
(74) *Attorney, Agent, or Firm* — Oblon, Spivak, McClelland, Maier & Neustadt, L.L.P.

(57) ABSTRACT

A method for acquiring hair characteristic data includes an image acquiring step and a data acquiring step. The image acquiring step acquires a cross-sectional image of a human hair 50, in which plural types of fibrous tissues (ortho cell 52a, para cell 52b) constituting cortex cells 52 contained in the human hair 50 are visualized so as to be distinguishable from each other. The data acquiring step acquires numerical information indicating a distribution state of the visualized plural types of fibrous tissues (ortho cell 52a, para cell 52b) from the cross-sectional image.

14 Claims, 21 Drawing Sheets

(51) Int. Cl.
*A61B 5/107* (2006.01)
*A61B 5/00* (2006.01)
*G01N 21/65* (2006.01)
*G01N 21/84* (2006.01)
*G01N 21/35* (2014.01)

(52) U.S. Cl.
CPC ...... *G01N2223/05* (2013.01); *G01N 2223/612* (2013.01); *G01N 21/35* (2013.01)
USPC ........... 382/128; 382/100; 382/115; 382/132; 382/133

(56) References Cited

U.S. PATENT DOCUMENTS

| | | | |
|---|---|---|---|
| 8,494,227 B2* | 7/2013 | Prokoski | 382/115 |
| 2009/0069541 A1* | 3/2009 | Kelly et al. | 530/357 |
| 2010/0106679 A1* | 4/2010 | Yamaguchi et al. | 706/54 |

OTHER PUBLICATIONS

Parbhu, Disulfide bonds in the outer layer of Keratin Fibers Confer higher Mechanical rigidity, 1999, Biochemistry 1999, 38, 11755-11761.*

Warren G. Bryson, and Ratneshwar Lal, Disulfide Bonds in the Outer Layer of Keratin Fibers Confer Higher Mechanical Rigidity: Correlative Nano-Indentation and Elasticity Measurement with an AFM, Biochemistry 1999, 38, 11755-11761.*

Bryson et al, Cortical cell types and intermediate filament arrangements correlate with fiber curvature in Japanese human hair, Journal of structural biology 166 (2009) 46-58.*

Roland De La Mettrie, Shape Variability and Classification qf Human Hair: A Worldwide Approach, [t~ImaH Biology, Jun. 2007, Vr 79, laO. 3, pp. 265-281.*

International Preliminary Report on Patentability and Written Opinion issued Mar. 22, 2012, in International Application No. PCT/JP2010/004714 (English translation).

Roland De La Mettrie, et al., "Shape Variability and Classification of Human Hair: A Worldwide Approach", Human Biology, vol. 76, No. 3, Jun. 2007, pp. 265-281.

Clarence R. Robbins, "Chemical and Physical Behavior of Human Hair", 4$^{th}$ Edition, Springer-Verlag, 2002, pp. 386-473.

J. A. Swift, "Morphology and histochemistry of human hair", Birkhauser Verlag, Basel, 1997, pp. 149-175.

Warren G. Bryson, et al., "Cortical cell types and intermediate filament arrangements correlate with fiber curvature in Japanese human hair", Journal of Structural Biology , vol. 166, No. 1, Apr. 2009, pp. 46-58.

* cited by examiner

METHOD FOR ACQUIRING HAIR CHARACTERISTIC DATA AND APPARATUS FOR ACQUIRING THE SAME

CROSS REFERENCE TO RELATED APPLICATION

This application is a 371 of PCT/JP10/004714, filed on Jul. 23, 2010, and claims priority to Japanese Patent Application No. 2009-181066, filed on Aug. 3, 2009.

TECHNICAL FIELD

The present invention relates to a method for acquiring hair characteristic data, and an apparatus for acquiring the hair characteristic data.

BACKGROUND ART

In general, the curl radius, the curl curvature and the like have been used as an index for objectively describing the degree of a curly hair (Non-patent Document 1). Further, the thickness of the hair, elasticity against the tension, bending stress and the like have been used as an index for objectively describing hair properties concerning a feel such as tensile properties, elastic properties, and softness of the hair (Non-patent Document 2).

In general, the curl radius and the curl curvature can be calculated by an actual measurement of the entire curved shape of a single hair. As a method for evaluating a curly hair, there has been known a method for analyzing penetration speed of an organic substance or inorganic salt to the hair (Patent Document 1). Further, there is proposed a method for evaluating the degree of curl of the hair by focusing on a bunch of fibrous tissues constituting cortex cells, and obtaining a ratio of absorbance of amide I (C=O bond) contained in this bunch to that of amide II (N—H bond) on the basis of a cross-sectional image of the hair (Patent Document 2).

Human hairs (scalp hair) are mainly formed by scaly (layered) cuticle cells covering the surface of the hair, fibrous cortex cells mainly forming the interior of the hair, and medulla cells constituting porous medulla existing at the central part of the hair. It is said that, of these cells, the cortex cell existing in the hair has at least two types: a cell similar to a para cortex cell of wool and a cell similar to an ortho cortex cell of wool (Non-patent Document 3).

Non-patent Document 3 describes a relationship between the abundance ratio of these two types of cortex cells and a shape of the hair. More specifically, it categorizes the hair into the Asian hair (Mongoloid), the Caucasian hair (Caucasoid), and the Ethiopian hair (African), and describes that there is a certain tendency between a variation of curl of the hair depending on the races and the abundance ratio of the two types of cortex cells.

Details of Non-patent Document 4 will be described later.

RELATED DOCUMENTS

Patent Documents

Patent Document 1: Japanese Patent Publication No. JP-A-H9-178738
Patent Document 2: Japanese Patent Publication No. JP-A-2006-170915

Non-Patent Document

Non-patent Document 1: R. De la Mettrie, et al., Human Biology, Vol. 79 No. 3, pp. 265-281, 2007
Non-patent Document 2: C. R. Robbins, "Chemical and Physical Behavior of Human Hair" 4th Ed., Springer-Verlag New York, Inc., pp. 386-473, 2002
Non-patent Document 3: "Morphology and histochemistry of human hair" in "Formation and Structure of Human Hair," J. A. Swift, P. Jolles, H. Zahn, and H. Hocker, Eds., Birkhauser Verlag, Basel, pp. 149-175, 1997
Non-patent Document 4: W. G. Bryson, et al., Journal of Structural Biology, Vol. 166, pp. 46-58, 2009

SUMMARY OF THE INVENTION

Problems to be Solved by the Invention

With the evaluation methods described in Patent Documents 1 and 2, the cortex cell is not separated into plural types to evaluate the cell, and hence, it is difficult to accurately quantify the hair characteristics.

Further, although indicating that the abundance ratios of the plural types of the cortex cells constituting the human hair contribute to the hair characteristics in a certain degree, Non-patent Document 3 does not provide any quantitative consideration for describing the hair characteristics.

The present invention has been made in view of the problems described above and provides a method for and an apparatus for simply acquiring quantitative information for describing the hair characteristics.

Means for Solving the Problem

A method for acquiring hair characteristic data according to the present invention includes: acquiring a cross-sectional image of a human hair, in which plural types of fibrous tissues constituting cortex cells contained in the human hair are visualized in such a manner as to be distinguishable from each other; and, acquiring, from the cross-sectional image, numerical information indicating a distribution state of the visualized plural types of fibrous tissues.

Further, an apparatus for acquiring hair characteristic data, including: an image acquiring unit that acquires a cross-sectional image of a human hair, in which plural types of fibrous tissues constituting cortex cells contained in the human hair are visualized in such a manner as to be distinguishable from each other; and, a data acquiring unit that acquires, from the cross-sectional image, numerical information indicating a distribution state of the visualized plural types of fibrous tissues.

It should be noted that, in the invention described above, the term "cross-sectional image of the human hair" means an image obtained by capturing an image of all or a part of a cross section intersecting an axis of the human hair (cross section in the lateral direction). The cross-sectional image of the human hair may be an image of a physical cutting plane of the human hair, or may be a transparent image, as long as it is possible to recognize the distribution states of the tissues in the radial direction of the fibrous tissues constituting the cortex cells of the target hair.

Further, the state where plural types of the fibrous tissues are visualized in the cross-sectional image of the hair in a manner that can be distinguished from each other means a state where the plural types of the fibrous tissues can be visually distinguished from each other or can be distinguished from each other through an image processing means.

It should be noted that the constituent elements (units) of the present invention do not necessarily exist independently. The constituent elements (units) of the present invention may be formed, for example, such that plural constituent elements form one unit; one constituent element is formed by plural units; one constituent element constitutes a part of the other constituent element; and, a part of one constituent element overlaps with a part of the other constituent element.

Effect of the Invention

With a technique of acquiring hair characteristic data according to the present invention, the distribution states of the fibrous tissues constituting the cortex cells are acquired as the numerical information, so that it is possible to quantitatively evaluate the hair characteristic, or objectively select an appropriate hair treatment method or a hair-care agent.

BRIEF DESCRIPTION OF THE DRAWINGS

The above-described object and other objects of the present invention, and features and advantages of the present invention will be made further clear by the preferred embodiment described below and the attached drawings described below.

DESCRIPTION OF EMBODIMENTS

Figure 1:
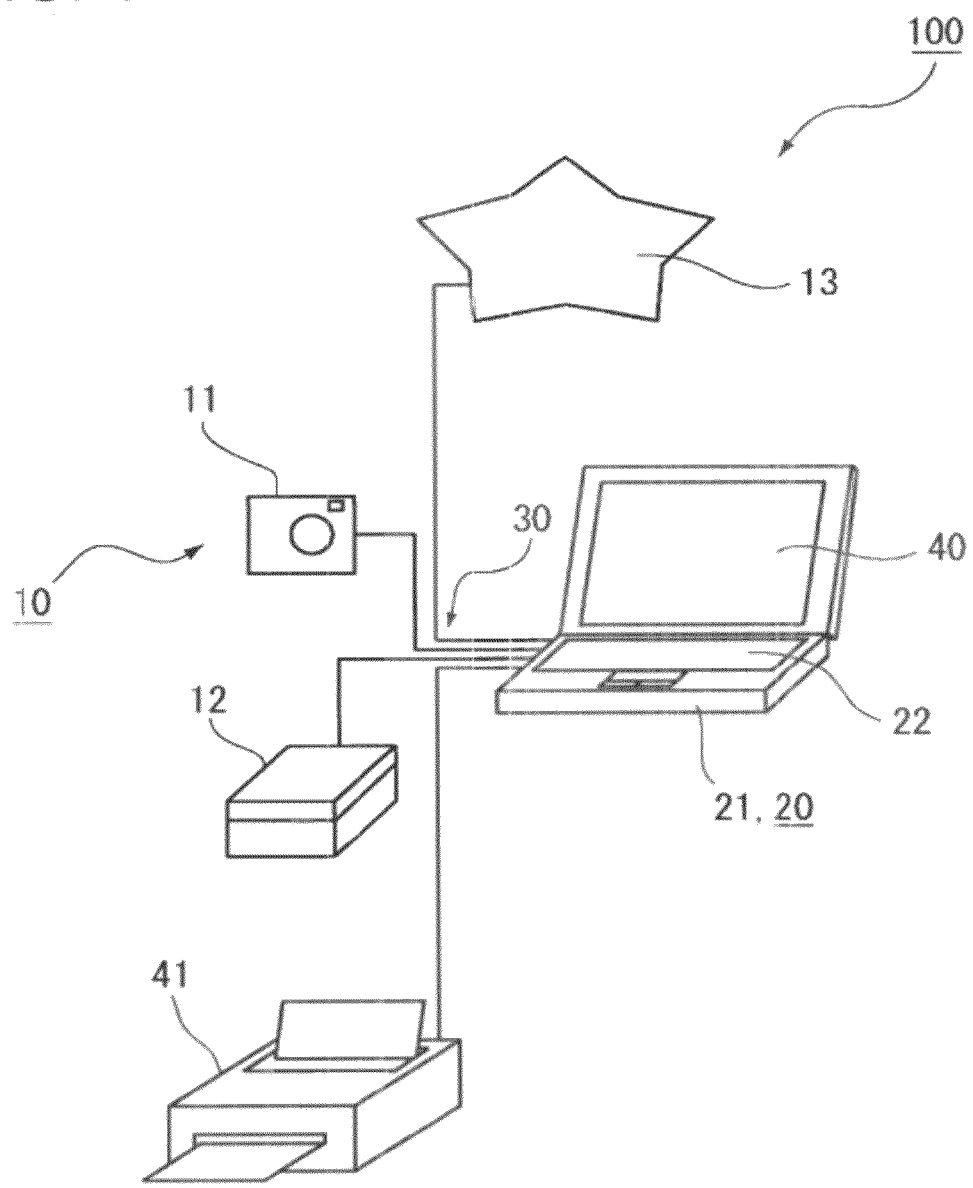
FIG. 1 is a block diagram illustrating one example of a data acquiring apparatus according to a first embodiment of the present invention.

Hereinbelow, embodiments of the present invention will be described with reference to the drawings. Note that, in all the drawings, the same constituent components are denoted with the same reference numerals, and detailed explanation thereof will not be repeated.

First Embodiment

FIG. 1 is a block diagram illustrating one example of a apparatus (data acquiring apparatus 100) for acquiring hair characteristic data according to this embodiment.

First, the data acquiring apparatus 100 according to this embodiment will be generally described.

The data acquiring apparatus 100 includes an image acquiring unit 10 that acquires a cross-sectional image of a hair, in which plural types of fibrous tissues constituting cortex cells of a human hair are visualized in such a manner as to be distinguishable from each other, and a data acquiring unit 20 that acquires, from the cross-sectional image, numerical information indicating distribution states of the visualized plural types of fibrous tissues.

The data acquiring apparatus 100 exemplified in FIG. 1 is connected through a communication line 30 to a digital camera 11 serving as the image acquiring unit 10, and a personal computer body 21 serving as the data acquiring unit 20.

The image acquiring unit 10 acquires a cross-sectional image of a human hair (not illustrated in FIG. 1) and transmits the acquired image to the data acquiring unit 20. Various means can be used as the image acquiring unit 10 and the digital camera 11 is one example of the various means.

As the image acquiring unit 10, it may be possible to use an image scanner 12 in place of the digital camera 11. In other words, it may be possible to take the cross-sectional picture of the hair, convert it into image information through the image scanner 12, and transmit it to the data acquiring unit 20.

Further, as the cross-sectional image of the hair, it may be possible to transmit a cross-sectional image stored in a not-illustrated web server through the Internet 13 or the communication line 30 to the data acquiring unit 20. In this case, the web server and the Internet 13 function as the image acquiring unit 10.

More specifically, the data acquiring unit 20 according to this embodiment is the personal computer body 21 including a predetermined calculation function to function as a calculation unit and a storage unit. The data acquiring unit 20 includes a keyboard 22 serving as an information input unit, and a display 40 serving as an information output unit.

The information output unit outputs the distribution states of the fibrous tissues constituting the cortex cells and evaluation results of the hair characteristic.

As the information output unit, it may be possible to use a printer 41 or the Internet 13 connected through the communication line 30 to the data acquiring unit 20, in addition to or in place of the display 40.

Next, a method for acquiring the hair characteristic data according to this embodiment (hereinafter, also referred to as the present method) will be described in detail.

The present method includes an image acquiring step and a data acquiring step.

The image acquiring step includes acquiring the cross-sectional image of the human hair in which plural types of fibrous tissues constituting cortex cells contained in the human hair are visualized in such a manner as to be distinguishable from each other.

The data acquiring step includes acquiring, from the cross-sectional image, numerical information indicating the distribution states of the visualized plural types of fibrous tissues.

Next, each of the steps will be described in detail.

[Image Acquiring Step]

In this step, a cross-sectional image of a hair of a given subject is captured to acquire information indicative of cell morphology, structure, property, protein composition, or chemical composition and so on inside the hair, as image information, information indicating.

More specifically, the image acquiring step includes a step (a visualization step) of visualizing the plural types of the fibrous tissues constituting the cortex cells contained in the human hair in a manner that the visualized plural types of the fibrous tissues can be distinguishable from each other, and a step (an imaging step) of capturing the cross-sectional image of the hair.

Specific examples of the image acquiring step will be described later. The order of performing the visualization step and the imaging step is not specifically limited, and these steps may be performed at the same time.

More specifically, the cross-sectional image of the hair may be acquired by the image acquiring unit 10 in a state where the fibrous tissues are visualized in advance so as to be distinguishable from each other by the visualization step such as staining of the cross section of the hair. In this case, the imaging step is performed by the image acquiring unit 10 after the visualization step. This case corresponds to a staining method and a gene observation method described later.

Further, it may be possible to perform the visualization step to the cross section of the hair and the imaging step of the cross-sectional image at the same time. This case corresponds to a spectrum measurement method and an X-ray scattering method.

Further, for a hair in a state where fibrous tissues of the hair cannot be visually distinguishable from each other, it may be possible to distinguishably visualize the fibrous tissues by capturing the cross-sectional image of the hair by the image acquiring unit 10, and then, subjecting the captured image to image processing. In this case, the imaging step is performed by the image acquiring unit 10 and the visualization step is performed by the data acquiring unit 20. This case corresponds to a TEM observation method and a microprobe observation method described later.

Figure 2:
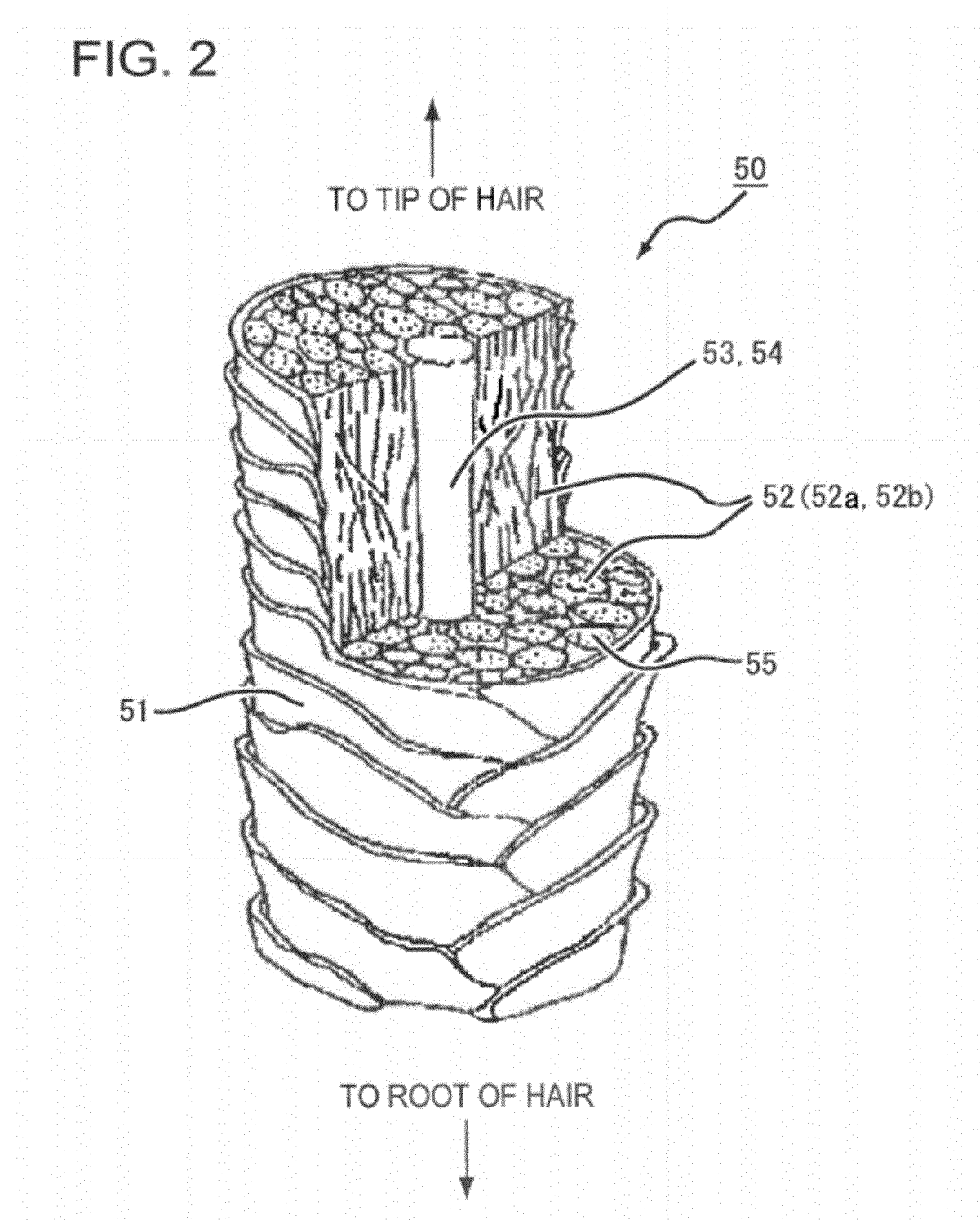
FIG. 2 is a schematic view of a cross section of a human hair.

Next, a structure of the human hair will be described. FIG. 2 is a schematic view of a cross section of a part of a hair 50 of a human.

As illustrated in FIG. 2, the hair 50 includes scaly (layered) cuticle cells 51 covering the surface of the hair 50, fibrous cortex cells 52 occupying the major part of the inside of the hair 50, and medulla cells 54 constituting a medulla 53 existing at the central portion of the hair.

The medulla 53 of a hair of the Japanese people is more likely to have porous and sponge-like forms. Further, the wool is formed mainly by the cuticle cells 51 and the cortex cells 52, and in most cases, is different from the human hair in that the wool does not contain the medulla 53.

The cortex cells 52 occupy the major part of the human hair, and contain cells and an intercellular connection substance. The cortex cells 52 contains ortho cells 52a and para cells 52b, which will be described later, and variant cortex cells. The ortho cells 52a and the para cells 52b each constitute a fibrous structure around the medulla 53.

The cortex cell 52 has a configuration in which fibrous units called a macrofibril 55 and having a diameter in the approximate range of 0.1 to 0.6 μm gather in a bundled manner.

The macrofibril 55 has a configuration in which intermediate filaments (IF) having a narrower diameter (about 7 nm in diameter) gather in a bundled manner.

In the present invention, the para cell 52b refers to a cell among the cortex cells 52 of the human hair 50, in which plural macrofibrils 55 in the cortex cell are integrated to form a relatively large domain in the order of micron. In the macrofibril 55 constituting the para cell 52b, a large number of intermediate filaments (IF) are oriented substantially in parallel in the axial direction of the hair.

The ortho cell 52a refers to a cell among the cortex cells 52, in which plural macrofibrils 55 having a size of the submicron order gather in a manner that each maintains their own formations. In the macrofibril 55 constituting the ortho cell 52a, the IFs are oriented obliquely in a spiral form.

Therefore, it is possible to visualize the ortho cell 52a and the para cell 52b in a manner that they can be distinguished from each other on the basis of the size of the macrofibril 55 and the orientation of the IF.

Further, since the para cell 52b is oriented substantially in a straight manner along the axis of the hair, it has a higher tensile modulus of elasticity as compared with the ortho cell 52a.

It should be noted that, from the viewpoint of the formation of the macrofibril and the structure of the IF orientation, the para cell 52b of the human hair 50 has a structure similar to that of the para cortex cell or meso cortex cell of the wool, and, the ortho cell 52a of the human has a structure similar to that of the ortho cortex cell of the wool. However, the contained components and properties are different between the ortho cell 52a of the human hair 50 and the ortho cortex cell of the wool, and between the para cell 52b of the human hair 50 and the para cortex cell or meso cortex cell of the wool. Further, as described above, the occupancy rate of the medulla is significantly different between the human hair and the wool. Therefore, it is difficult to estimate the relationship between the composition of the cortex cell of the human hair and the hair characteristic of the human hair on the basis of the relationship between the composition of the cortex cell of the wool and the hair characteristic.

Next, plural specific examples of the image acquiring step will be described in detail.

[Image Acquiring Method 1: Staining Method]

The first example of a method performed in the image acquiring step includes a method for staining the cross section of the hair 50 with one type, or two or more types of staining agents to distinguishably visualize the plural types of fibrous tissues (ortho cell 52a, and para cell 52b).

The cuticle cell 51, the two types of the cortex cells (ortho cell 52a and para cell 52b), and the medulla cell 54 existing in the human hair 50 have different protein compositions and different formations from each other, and hence, staining properties thereof vary depending on the types of staining agents. Therefore, by employing appropriate staining agents, it is possible to acquire the cross-sectional image reflecting the distribution state of each of the cells.

There is not specific limitation on the staining agent employed in this method, provided that it colors only one of the ortho cell 52a and the para cell 52b. Further, by using an agent staining substantially only the ortho cell 52a and an agent staining only the para cell 52b, in other words, by using the combination of two or more types of staining agents, it is possible to clearly distinguish the cells from each other. However, considering the effect of the color of hair, it is preferable to employ a fluorescent dye having a fluorescence wavelength range different from the fluorescence resulting from the components of the hair. More specifically, by employing sulforhodamine having an orange fluorescence for the ortho cell 52a, and fluorescein having a yellow-green fluorescence or alkali metal salt thereof for the para cell 52b, it may be possible to stain only the target cell into a desired color.

[Image Acquiring Method 2: TEM Observation Method]

The second example of a method performed in the image acquiring step includes a method for acquiring the cross-sectional image reflecting the distribution states of the cells constituting the plural types of fibrous tissues (ortho cell 52a and para cell 52b), by observing the hair 50 with a transmission electron microscope (TEM).

The cuticle cell 51, the two types of the cortex cells (ortho cell 52a and para cell 52b), and the medulla cell 54 have different protein compositions and different formations, and hence, are stained differently depending on the types of electronic staining agent used in the transmission electron microscope. Therefore, it is possible to acquire the cross-sectional image in a manner that reflects the distribution state of each of the cells on the basis of the differences in the formation of each of the cells to be observed using the transmission electron microscope.

[Image Acquiring Method 3: Spectrum Measurement Method]

The third example of a method performed in the image acquiring step includes a method for visualizing the plural types of the fibrous tissues (ortho cell 52a and para cell 52b) in a manner that they can be distinguished in the cross-sectional image from each other, by measuring infrared absorption spectrum or Raman spectrum of the cross section of the hair 50.

The cuticle cell 51, the two types of the cortex cells (ortho cell 52a and para cell 52b), and the medulla cell 54 have different protein compositions and different formations, and hence, have different infrared absorption properties at the time of the measurement with a Fourier transform infrared spectroscopy (FT-IR). Therefore, by selecting appropriate infrared signals, it is possible to acquire the cross-sectional image reflecting the distribution state of each of the cells on the basis of the intensity of the signals or the ratio of plural signal intensities.

Further, the cuticle cell 51, the two types of the cortex cells (ortho cell 52a and para cell 52b), and the medulla cell 54 have different Raman spectrums, which are obtained by emitting the polarized excitation laser. Thus, by selecting appropriate Raman spectrum band, it is possible to acquire the cross-sectional image reflecting the distribution state of each of the cells on the basis of the intensity of the signals or the ratio of plural signal intensities.

[Image Acquiring Method 4: Microprobe Observation Method]

The fourth example of a method performed in the image acquiring step includes a method for acquiring the cross-sectional image reflecting the distribution states of the plural types of the fibrous tissues (ortho cell 52a and para cell 52b), by observing the cross section of the hair 50 with a microprobe microscope. The microprobe microscope is a general name of a microscope for obtaining information on a fine area on a surface by moving a probe having a sharply formed top end on a cross section of the hair, which is a sample to be measured. An example of the microprobe microscope used in this method includes an atomic force microscope (AFM).

The cuticle cell 51, the two types of the cortex cells (ortho cell 52a and para cell 52b), and the medulla cell 54 have different protein compositions and different structures, Thus, it is possible to acquire the cross-sectional image reflecting the distribution state of each of the cells on the basis of the properties and formations observed with the microprobe microscope.

[Image Acquiring Method 5: X-Ray Scattering Method]

The fifth example of a method performed in the image acquiring step includes a method for acquiring the cross-sectional image reflecting the distribution states of the plural types of the fibrous tissues (ortho cell 52a and para cell 52b), by observing the X-ray scattered image of the hair 50 with a microbeam X-ray.

The cuticle cell 51, the two types of the cortex cells (ortho cell 52a and para cell 52b), and the medulla cell 54 have different microstructures from each other, and hence, have different X-ray scattered images. Therefore, by using the microbeam X-ray, it is possible to acquire the cross-sectional image reflecting the distribution state of each of the cells on the basis of difference in the X-ray scattered images.

[Image Acquiring Method 6: Gene Observation Method]

The sixth example of a method performed in the image acquiring step includes a method for acquiring the cross-sectional image reflecting the distribution states of the plural types of the fibrous tissues (ortho cell 52a and para cell 52b), by observing the behavior of gene expression in the hair follicle of the human.

The cuticle cell 51, the two types of the cortex cells (ortho cell 52a and para cell 52b), and the medulla cell 54 have different protein compositions, and hence, genes (mRNA) expressing in the hair follicle are different between these cells. Thus, by observing the behavior of the gene expression in the hair follicle, it is possible to acquire the cross-sectional image reflecting the distribution state of each of the cells on the basis of difference in gene expressions.

The image acquiring step may be performed by selecting one or more of the above described methods.

Of the methods described above, it is preferable to employ the staining method using the fluorescent dye, the TEM observation method, the spectrum measurement method (infrared absorption spectrum method), the microprobe observation method, the X-ray scattering method, and the gene observation method from the viewpoint of insusceptibility to the effect of the hair color. Further, from the viewpoint of spatial resolution, it is preferable to employ the staining method, the TEM observation method, the microprobe observation method, the X-ray scattering method, and the gene observation method. Yet further, from the viewpoint of simplicity, it is preferable to employ the staining method, the spectrum measurement method (infrared absorption spectrum method and Raman spectrum method), and the microprobe observation method.

With the above-described methods, it is possible to obtain the image information reflecting the distribution states of the four types of cells including the cuticle cell 51, and the two types of the cortex cells (ortho cell 52a and para cell 52b), and in some cases, further including the medulla cell 54. Hereinafter, the term "four types of cells" refers to the cuticle cell 51, the ortho cell 52a, the para cell 52b, and the medulla cell 54 unless otherwise specified.

[Data Acquiring Step]

In this step, numerical information indicating the distribution states of the plural types of fibrous tissues (ortho cell 52a and para cell 52b) is acquired with an image analysis applied to the captured cross-sectional image.

More specifically, the data acquiring step includes a step (an analyzing step) of subjecting the captured cross-sectional image to the image analysis, and a step (a quantification step) of acquiring the numerical information on the basis of the results of the image analysis.

[Analyzing Step]

In the analyzing step, the distribution of, for example, the four types of cells existing in the human hair is converted into an image through digital processing of the cross-sectional image and the like.

Here, the cuticle cell 51, the cortex cell 52, and the medulla cell 54 can be easily distinguished from each other in the cross-sectional image of the hair 50 on the basis of the difference in the cell shape and the like. For example, the cuticle cell 51 exists on the surface of the hair 50 in a layered manner. Thus, on the basis of the formation of the cuticle cell 51, it is possible to distinguish the cuticle cell 51 from the cortex cell 52 in an automatic manner. Further, the medulla cell 54 existing at the central portion of the hair 50 is formed in a porous form, especially in the case of the Japanese. Thus, it is possible to distinguish the medulla cell 54 from the cortex cell 52 in an automatic manner on the basis of its formation.

The two types of the cortex cells 52 including the ortho cell 52a and the para cell 52b have different formations in the order of submicron. Thus, in the case where the spatial resolution of the cross-sectional image is not more than submicron order, the ortho cell 52a and the para cell 52b can be distinguished from each other on the basis of the difference in their formations.

Even in the case where the spatial resolution of the cross-sectional image exceeds the submicron order, if the acquired image information reflects the structures or protein compositions of the cells, it is possible to distinguish between the ortho cell 52a and the para cell 52b on the basis of the information reflecting them. For example, by entirely coloring or contouring the ortho cell 52a and the para cell 52b through the staining method, the spectrum measurement method, the X-ray scattering method and the like, it is possible to distinguish between the ortho cell 52a and the para cell 52b on the basis of the difference in the color information or pattern shapes.

In order to obtain the clear image of the distribution states of the distinguished four types of cells through digital processing, the data acquiring unit 20 (see FIG. 1) may apply plural colors to the respective cells through the image processing.

[Quantification Step]

There is not any specific limitation on the numerical information acquired in the quantification step in this method, and various parameters may be selected for quantitatively describing the hair characteristic.

More specifically, as examples of the numerical information, this embodiment employs (i) distance between centroids of the fibrous tissues, (ii) abundance ratio of the fibrous tissue, (iii) second moment of area of the para cell, and (iv) the degree of dispersion of the fibrous tissue. The (i) through (iv) described above will be described in detail.

The term "distance between centroids of the fibrous tissues" as used in this embodiment refers to a distance between a centroid of one fibrous tissue (ortho cell 52a) and a centroid of the other fibrous tissue (para cell 52b) in the cross-sectional image.

Further, the term "abundance ratio of the fibrous tissues" refers to an abundance ratio of the fibrous tissue (any one of the ortho cell 52a and the para cell 52b) relative to the cortex cell 52.

Further, the term "second moment of area of the para cell 52b" as used in this embodiment refers to a second moment of area in the weak axis direction in the cross-sectional image.

Further, the term "degree of dispersion of the fibrous tissue" refers to the degree of mixture of one fibrous tissue (ortho cell 52a) with the other fibrous tissue (para cell 52b).

(i) Distance Between Centroids of the Fibrous Tissues

The shapes and properties of the hair 50 vary depending on positions where the four types of cells exist in the human hair. However, of the four types of cells, the cuticle cell 51 is located in the vicinity of the surface of the hair regardless of the type of hair, and if existing, the medulla cell 54 is located in the vicinity of the center of the hair. Thus, the difference resulting from the positions of the cuticle cell 51 and the medulla cell 54 is small between the hairs 50. This reduces the effect of positional differences of the cuticle cell 51 and the medulla cell 54 on the shapes and properties of the hair 50.

On the other hand, the two types of cortex cells (ortho cell 52a and para cell 52b) are distributed in the hair in various manners, and the shapes and properties of the hair vastly differ depending on the positions of these cells.

In particular, as a result of the study made by the present inventors, it is found that the distance between centroids of the ortho cell 52a and the para cell 52b positively correlates with the curl curvature, which is an index value indicating the degree of curl of the hair 50.

Therefore, it is effective to calculate the distance between centroids of the ortho cell 52a and the para cell 52b by obtaining the centroids of the distributions of the ortho cell 52a and the para cell 52b in the cross section as the value indicating the difference in positions of these two types of cortex cells, especially the unevenness of the distributions of the cells.

The distance between the centroids is near zero in the case where the ortho cell 52a and the para cell 52b are distributed in the cross section of the hair in a uniform or isotropic manner. On the other hand, the value becomes larger in the case where these cells are distributed nonuniformly in an uneven manner. Thus, it is possible to use the distance between centroids of the ortho cell 52a and the para cell 52b as a value indicating the degree of unevenness of the distribution of the ortho cell 52a and the para cell 52b.

More specifically, it is possible to calculate the coordinate average of pixels constituting the ortho cell 52a in the cross-sectional image of the hair 50, and obtain the position of the centroid (face center) of the ortho cell 52a. The same applies to the para cell 52b. Further, by calculating the distance between the centroid position of the ortho cell 52a and the centroid position of the para cell 52b, it is possible to obtain the distance between centroids of the ortho cell 52a and the para cell 52b.

(ii) Abundance Ratio of Fibrous Tissues

The four types of the cells have different constituent protein compositions, structures and formations, and have different micro-properties. Thus, the properties of the hair 50 differ according to the abundance ratio of these cells.

In particular, as a result of the study made by the present inventors, it is found that the abundance ratio of the para cell 52b in the cortex cell 52 positively correlates with the bending elastic modulus, which is an index value indicating the bending rigidity of the hair 50.

The abundance ratio of these cells can be obtained, for example, through the image analysis described below. More specifically, first, in the cross-sectional image of the hair 50, the areas occupied by the four types of the cells are each obtained by the summation of pixels contained in each of the four types of the cells. Then, the ratio of the area occupied by each of the cells relative to the total area of the four types of the cells (cross-sectional area of the hair 50) is calculated, respectively.

Further, the ratio of the area occupied by each of the ortho cell 52a and the para cell 52b relative to the total area occupied by the two types of the cortex cells 52 including the ortho cell 52a and the para cell 52b is obtained, respectively, and then, the abundance ratios of the respective cells can be calculated.

(iii) Second Moment of Area of the Fibrous Cells

The properties of the hair 50 differ according to the second moments of area of the ortho cell 52a and the para cell 52b in the cross-sectional image because of the difference in the properties of the ortho cell 52a and the para cell 52b. The para cell 52b has a higher tensile rigidity as compared with the ortho cell 52a, and hence, in general, the bending rigidity of the hair 50 increases as the second moment of area of the para cell 52b in the cross-sectional image becomes higher.

It should be noted that the bending of the hair 50 occurs in the weak axis direction. Therefore, it is preferable to set plural radial axes extending from the centroid of the hair 50, and calculate the second moment of area in each of the set axes. Then, by setting an axis direction indicating the minimum value to the weak axis direction, it is possible to obtain the second moment of area in this direction as the second moment of area of the para cell 52b.

More specifically, on the basis of the positions and areas of the pixels contained in the para cell 52b in the cross-sectional image of the hair 50, it is preferable to calculate the second moment of area of the desired axis direction.

(iv) Degree of Dispersion of the Fibrous Tissue

As a result of the study made by the present inventors, it is found that the osmosis property of a hair-care agent to the ortho cell 52a and the para cell 52b is faster in the ortho cell 52a, and slower in the para cell 52b. Therefore, in general, in the hair 50 having the para cell 52b with the lower dispersibility and having a larger domain of the para cell 52b, the osmosis of the hair-care agent to the inside of the domain of the para cell 52b is inhibited. The hair 50 having the para cell 52b with the higher dispersibility exhibits favorable penetration property of the hair-care agent.

Therefore, in the quantification step, it is preferable to obtain the degree of dispersion of the para cell 52b in the hair 50 through the quantification.

The degree of dispersion of the para cell 52b can be calculated through various methods.

The first method includes a method in which attention is paid to the ratio of area of small clusters of the para cell 52b. More specifically, calculation is made to obtain the total area of clusters having an area exceeding a predetermined threshold value of all the clusters (aggregated blocks) of the para cell 52b. Then, the ratio of the area occupied by small clusters each having an area less than the threshold value, relative to the total area of the para cell 52b is obtained as the degree of dispersion.

The second method includes a method of dividing the cross-sectional image of the hair 50 into segments to obtain an abundance ratio of the para cell 52b in each of the segments. More specifically, the cross-sectional image of the hair 50 is divided into segments passing through the centroid of the cross-sectional image and having radial shapes and equal areas, and pixels of the para cell 52b contained in each of the segments is counted. Then, by obtaining the average root mean square of the ratio of area of the para cell 52b in each of the segments, it is possible to quantify the degree of dispersion of the para cell 52b in the hair 50.

In addition to the method as described above, in the quantification step, it may be possible to obtain values concerning the physical form of the hair 50, such as the cross-sectional area, the flatness ratio (length of major diameter or minor diameter).

In this method, it may be possible to further obtain the numerical information indicating at least one of the distribution states of the cuticle cell 51 and the medulla cell 54 contained in the hair, in addition to that of the cortex cell 52.

In particular, it is preferable to obtain the numerical information indicating the distribution state of the cuticle cell 51 as well as that of the cortex cell 52.

The cuticle cell 51, the cortex cell 52, and the medulla cell 54 constituting the human hair 50 have largely different properties from each other, and hence, the characteristic of the hair 50 varies depending on the abundance ratios of these cells.

Further, the cuticle cell 51 has a higher amount of cystine and a higher density of disulfide bond in the cell as compared with the other cells, and hence, in general, is the hardest cell of all the three types of the cells described above. This cuticle cell 51 is located at a position further from the center of the hair in a manner that covers the surface of the hair, and hence, has a large effect especially on the bending stress and the torsional stiffness of the fiber of the hair.

Therefore, the hair having the larger amount of the cuticle cell 51 exhibits the higher bending stress and the higher torsional stiffness. This makes it possible to more accurately evaluate the hair characteristic by obtaining the distribution states of the cuticle cell 51 as well as the cortex cell 52 as the numerical information.

In this method, it may be possible to evaluate the shape (curvature) of the hair 50, or the mechanical properties of the hair fibers as the characteristics of the hair 50 on the basis of the obtained numerical information.

More specifically, in addition to the image acquiring step and the data acquiring step described above, it may be possible to further perform a reference acquiring step and an evaluation step.

In the reference acquiring step, calibration data indicating a relationship between the numerical information and the hair characteristic are obtained by using human hair samples as reference hairs.

In the evaluation step, the hair characteristic concerning the hair is evaluated on the basis of the numerical information of the hair acquired in the data acquiring step and the calibration data.

The reference acquiring step may be performed after the image acquiring step or the data acquiring step, or may be performed before these steps.

[Reference Acquiring Step]

In this step, the numerical information described above is obtained in advance by using as the reference hair the sample hair whose hair characteristics such as a modulus of elasticity are already known in advance. The number of the reference hair may be one, or may be two or more (a large number).

By acquiring the numerical information and the hair characteristic concerning the reference hair as reference point data or calibration data, it is possible to estimate the hair characteristics using the numerical information of the newly acquired target hair.

More specifically, by using a reference hair as a comparative reference, it may be possible to simply compare the hair characteristic of the target hair with that of the reference hair. Further, on the basis of the large number of reference hairs, a table or function is acquired in a data form using the relationship between specific numerical information and hair characteristic as a calibration line. It may be possible to estimate the characteristics of the hair on the basis of the numerical information of the target hair and the calibration line.

More specifically, for a large number of the reference hairs whose, for example, curl radius or curl curvature has been already known, the distance between centroids of the ortho cell 52a and the para cell 52b is calculated through an image analysis of the cross-sectional image. Then, a correlation function is preferably obtained by a statistical processing to a relationship between the curl radius or curl curvature and the distance between centroids of the ortho cell 52a and the para cell 52b.

[Evaluation Step]

In this step, the numerical information (distance between centroids of the ortho cell 52a and the para cell 52b) acquired from the cross-sectional image of the target hair 50 is applied, for example, to the above-described correlation function to obtain the curl radius or curl curvature, which is an index value indicating the degree of curl of the target hair 50.

It should be noted that, in this method, in lieu of the curl radius or curl curvature, it may be possible to obtain the bending elastic modulus and the abundance ratio of the para cell 52b of the large number of the reference hairs, and statistically calculate the correlation thereof.

Then, on the basis of the abundance ratio of the para cell 52b of the hair 50 to be evaluated, it may be possible to calculate the bending elastic modulus, which is an index value indicating the bending rigidity of the hair.

It should be noted that, in the data acquiring apparatus 100 illustrated in FIG. 1 and according to this embodiment, the reference acquiring step and the evaluation step can be performed by the data acquiring unit 20 (personal computer body 21). In this case, the calibration data are preferably stored in advance in the storage unit of the personal computer body 21.

[Output Step]

It is preferable that all or a part of the captured image of the hair 50, the cross-sectional image having each of the cells visualized, the acquired numerical information, and the information indicating the evaluation results are outputted from the data acquiring apparatus 100 through any manner. The cross-sectional image having the visualized hair 50 to be evaluated and the cross-sectional image having the visualized reference hair may be displayed next to each other.

As the output manner, it may be possible to use, for example, any of the display 40 of the personal computer body 21, a display connected to the personal computer body 21 through the communication line 30 or a wireless line, and an output from the printer 41.

It should be noted that it is only necessary that the constituent elements of the data acquiring apparatus 100 according to this embodiment are formed so as to be able to realize the functions thereof. For example, the data acquiring unit 20 may be realized, for example, by a dedicated hardware capable of achieving a predetermined function, a data processing apparatus having a predetermined function provided by a computer program, a predetermined function realized by a data processing apparatus through a computer program, and a combination thereof.

Further, the data acquiring apparatus 100 according to this embodiment may operate as, for example, hardware configured by general devices such as a central processing unit (CPU), a read only memory (ROM), a random access memory (RAM), and an interface (I/F) unit, or a dedicated logic circuit configured to carry out a predetermined processing operation, or a combination thereof, in a manner that can read out a computer program to carry out the corresponding processing operation.

With the technique of acquiring the hair characteristic data according to this embodiment, it is possible to obtain the parameters including the degree of curl of the hair largely affecting the gloss of the hair, the bending elastic modulus largely affecting the volume or softness of the hair, as the quantitative numerical information. Therefore, on the basis of the numerical information obtained from the target hair, it is possible to evaluate these characteristics of the hair, and provide objective information for assisting in selecting an appropriate hair treatment method or the hair-care agent.

With the conventional technique of actually measuring the entire curved shape of the hair and calculating the curl radius and the curl curvature, only one value can be obtained for each of the hair characteristic such as the curl radius, the curl curvature and the bending elastic modulus obtained from a single hair. On the other hand, with the technique of acquiring the hair characteristic data according to this embodiment, it is possible to calculate the hair characteristic for each of the length positions in the single hair by acquiring plural cross-sectional images and plural pieces of the numerical information from different length positions in the single hair. Therefore, according to this embodiment, it is possible to evaluate various aspects of the characteristics of the single hair.

Further, the conventional calculation method requires a predetermined length of hair to measure the hair characteristics. A tip of the single hair is formed by old cells. Thus, if the measurement of the hair characteristics is largely affected by the tip of the hair, the evaluated hair characteristic indicates characteristics of the old hair rather than the current state of the hair. On the other hand, according to this embodiment, it is possible to acquire the numerical information from the cross-sectional image of the root portion of the hair. This makes it possible to evaluate the hair characteristics concerning the properties of the current hair. Further, it is possible to predict the future hair characteristics such as the degree of the curly hair, the bending elastic modulus after the current hair grows.

EXAMPLES

Next, the present invention will be described in more detail on the basis of examples. In the following description, the reference characters of the elements correspond to those in FIG. 2 unless otherwise specified.

Example 1

Curly Hair

This example relates to a method of acquiring the numerical information describing the shape and the property of the hair by acquiring the cross-sectional image of the hair with the transmission electron microscope (TEM) and analyzing the acquired image.

[Acquiring Image Information]

With the transmission electron microscope (TEM), images of cross section of the hair subjected to electron staining using osmic acid and uranyl acetate were acquired, and the image information reflecting the distribution states of the cells in the hair on the basis of the difference in the formations of the cells was acquired.

As the target hair, a scalp hair of Caucasian female A in her thirties was sampled from the root of the hair in the vicinity of the scalp, the sampled scalp hair being not subjected to any chemical hair treatment such as perming, bleaching and hair coloring. The target hair was cut from the root with a length of about 12 mm to obtain a hair sample.

The prepared hair sample was cleaned with a shampoo, sufficiently rinsed with ion-exchange water, and then, dried. The dried hair sample was measured the curl radius, and it was found that the curl radius thereof was 0.9 cm. This value of the curl radius is classified into a curly hair.

After immersed into a O. 05M phosphate buffer solution (pH 6.7) containing 1.0 mass % of osmic acid for one hour to stain, the hair sample was rinsed with ion-exchange water to remove the excessive osmic acid, and was dried.

Next, the hair sample stained with osmic acid was embedded into an epoxy resin, cut out with a microtome to obtain a cross-sectional face of the hair with a thickness of 100 nm, and mounted on a copper mesh for the transmission electron microscope (TEM).

The cross section of the hair mounted on the copper mesh was immersed into a uranyl acetate solution with 2.0 mass % for four hours to stained, the excessive uranyl acetate was rinsed with the ion-exchange water, and then, the hair was dried. The cross section of the hair double-stained with osmic acid and uranyl acetate was observed with the transmission electron microscope (TEM), and then, an image of the cross section of the hair was obtained.

[Visualization of Cell Distribution]

Figure 3:
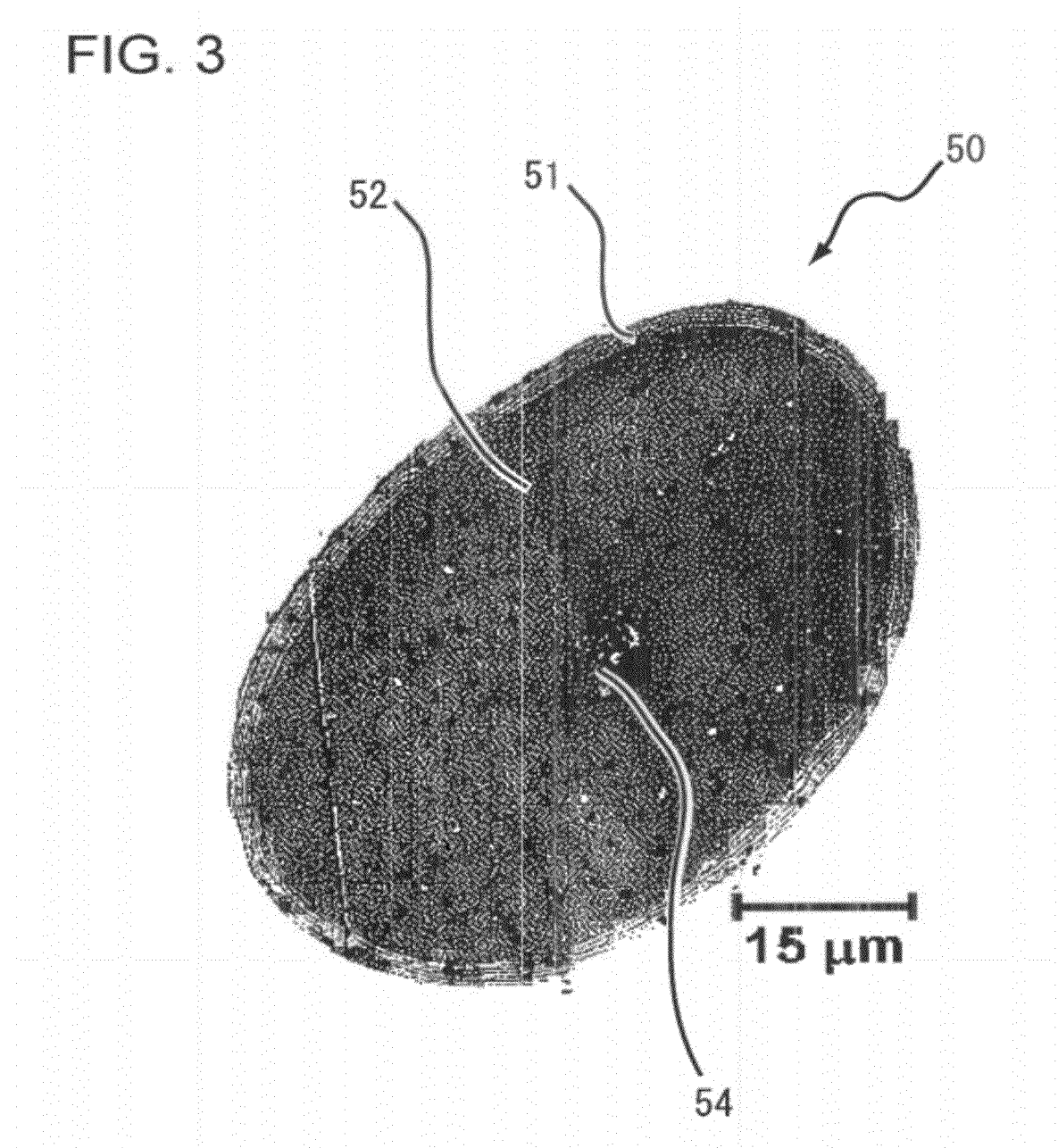
FIG. 3 is an overall image of a cross section of the hair of Example 1.

FIG. 3 illustrates an entire image of the cross section of the double-stained hair obtained by the observation with the transmission electron microscope (TEM).

FIG. 4 through FIG. 7 each illustrate a typical image of the cuticle cell 51, the para cell 52b, the ortho cell 52a, and the medulla cell 54 captured with a high magnification. In FIG. 3 through FIG. 7, a scale size is shown in each of the drawings. FIG. 3 is an image re-configured by integrating the high magnification images as illustrated in FIG. 4 through FIG. 7.

It should be noted that, in FIG. 3 through FIG. 7, black granular-like portions having a diameter of about 0.2 μm are melanin granules. Black portions having an indefinite shape are residues of nucleus of the cortex cell 52. White patches are cavities in the hair, or resins embedding and existing outside the hair.

Using the high magnification images of FIG. 4 through FIG. 7, the cuticle cell 51, the para cell 52b, the ortho cell 52a, and the medulla cell 54 were distinguished from each other, and the distinguished results were applied to FIG. 3.

Figure 4:
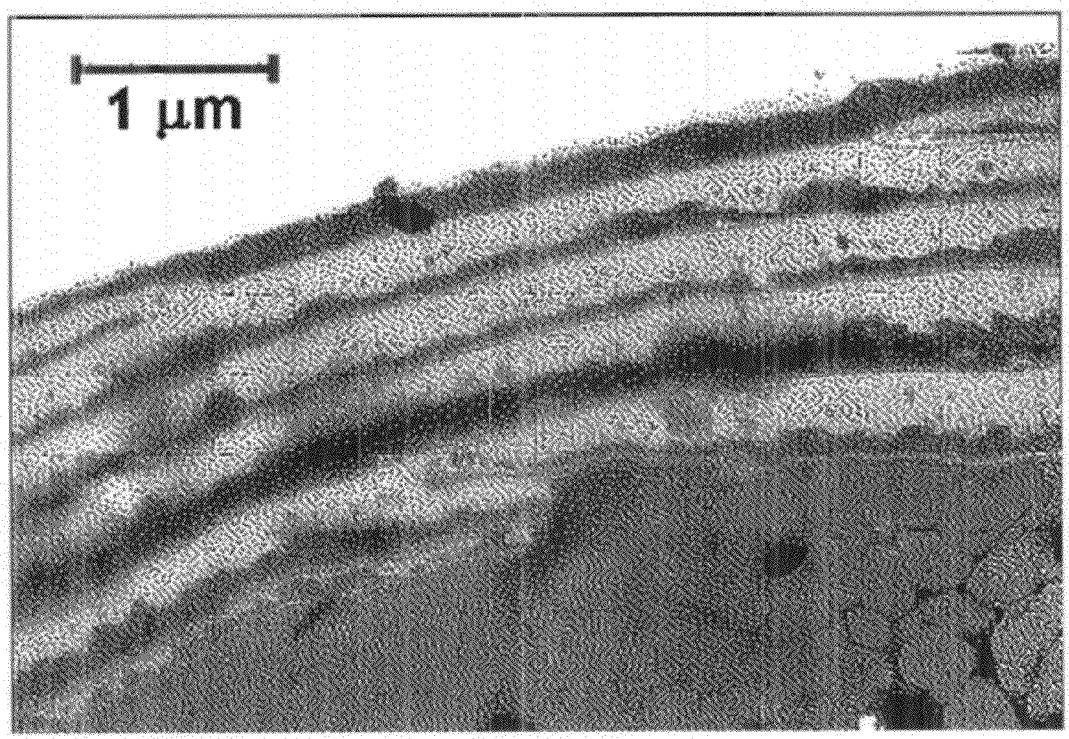
FIG. 4 is an enlarged view of FIG. 3, and illustrates cuticle cells.

As illustrated in FIG. 4, the cuticle cells 51 are located in the vicinity of the surface of the hair in a layered manner, and hence, on the basis of the difference in the formations thereof, it is possible to distinguish the cuticle cell 51 from the adjacent two types of the cortex cells 52 (para cell 52b and ortho cell 52a).

Figure 7:
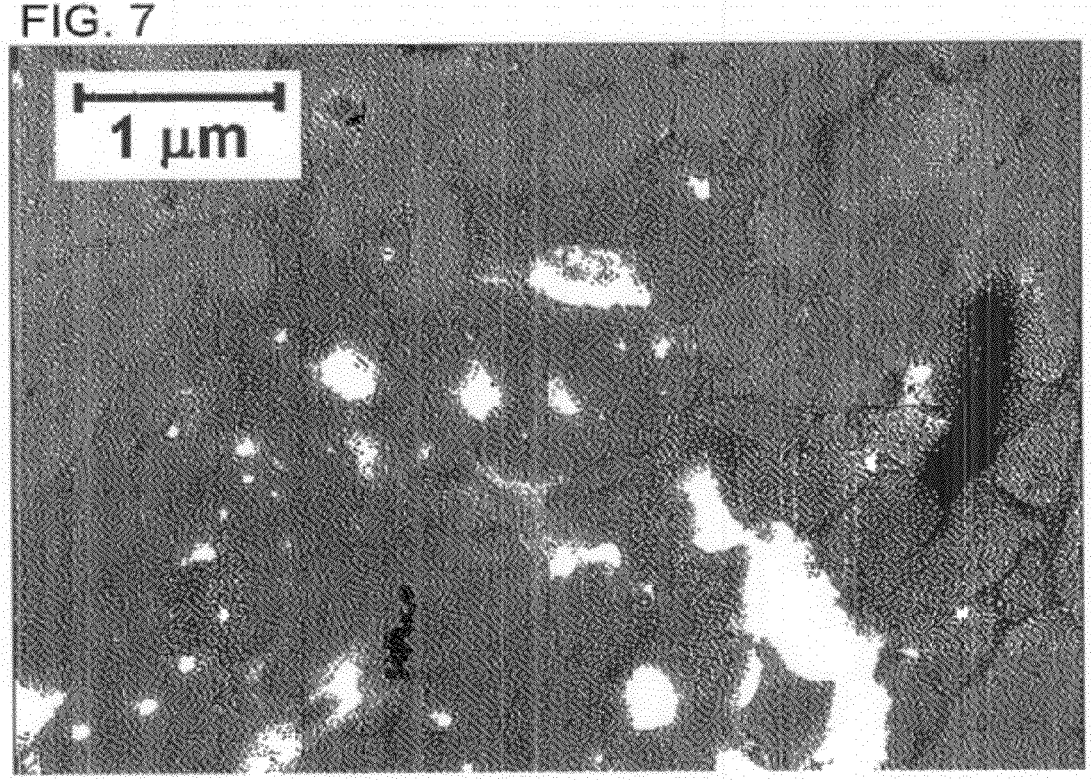
FIG. 7 is an enlarged view of FIG. 3, and a diagram illustrating medulla cells.

Further, as illustrated in FIG. 7, the medulla cell 54 is located at the center of the hair and has a porous structure, and hence, in a similar manner, on the basis of the difference in the formations thereof, it is possible to distinguish the medulla cell 54 from the two types of the cortex cells 52.

The two types of the cortex cells 52 including the para cell 52b and the ortho cell 52a have different formations in the order of submicron, and hence, it is possible to distinguish them from each other in an automatic manner on the basis of its formation.

Figure 5:
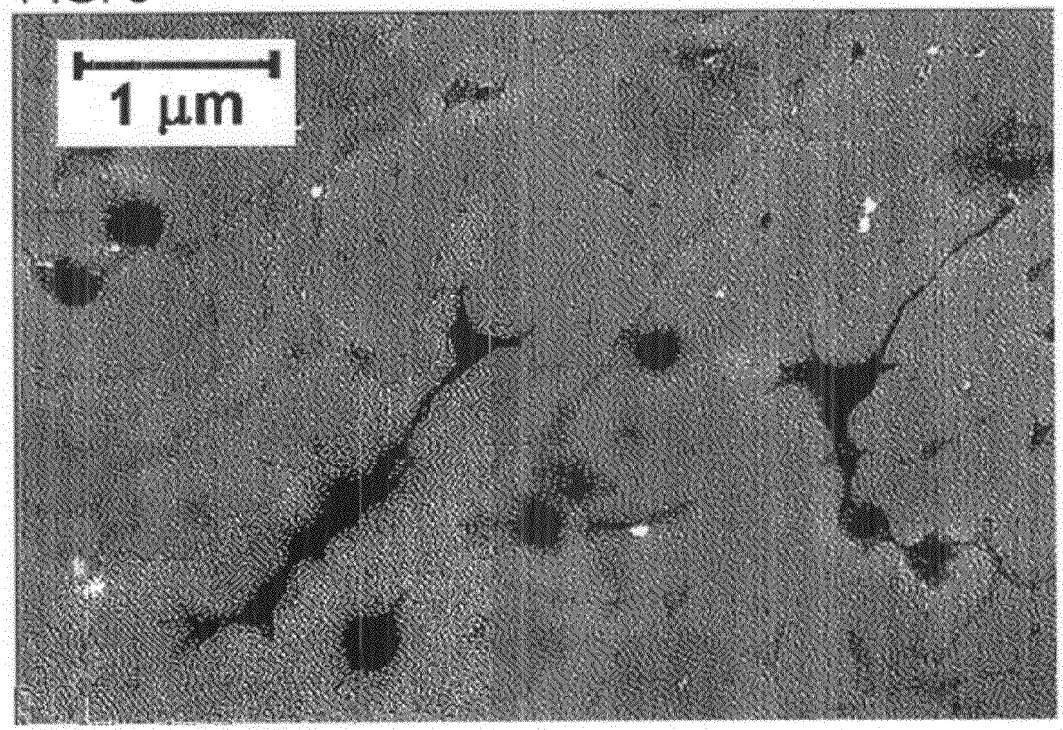
FIG. 5 is an enlarged view of FIG. 3, and a diagram illustrating a cell classified into a para cell (described in detail later) of cortex cells.

As illustrated in FIG. 5, in the para cell 52b, the macrofibrils are integrated to form a relatively large domain in the order of micron.

Figure 6:
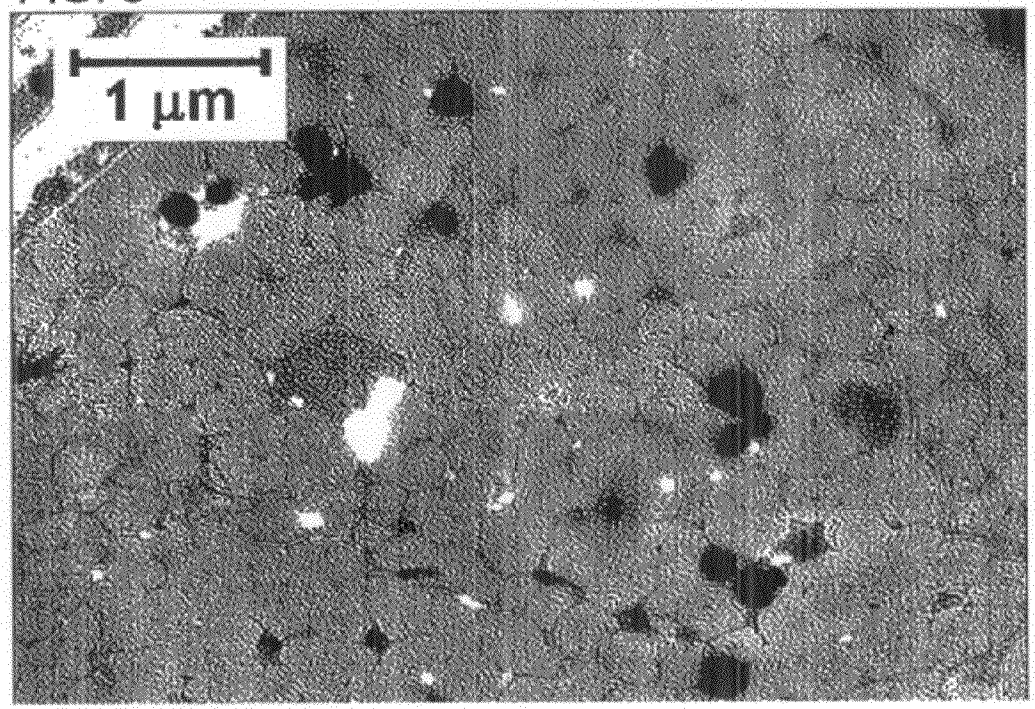
FIG. 6 is an enlarged view of FIG. 3, and a diagram illustrating a cell classified into an ortho cell (described in detail later) of cortex cells.

On the other hand, as illustrated in FIG. 6, the ortho cell 52a has a formation in which macrofibrils having a size of submicron order gather.

On the basis of the difference in the formations of the macrofibrils, it is possible to distinguish between the para cell 52b and the ortho cell 52a.

Figure 8:
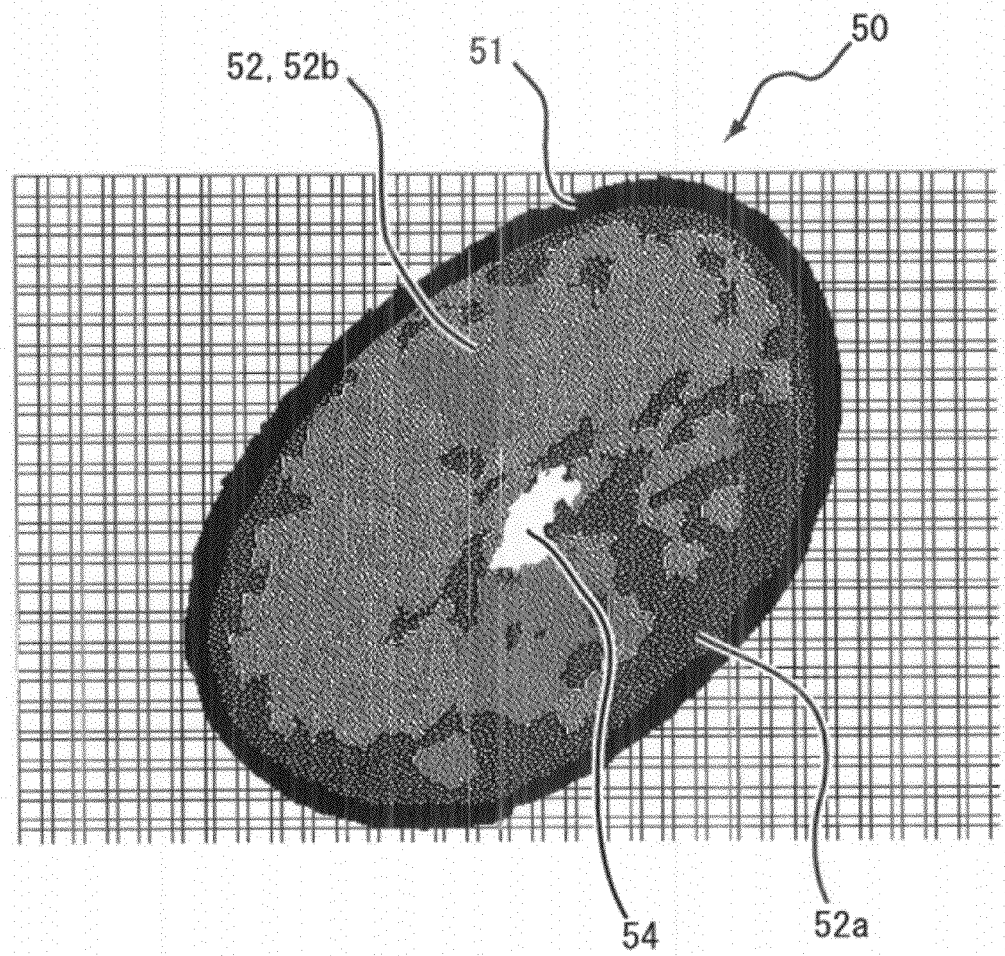
FIG. 8 is a visualized image of Example 1.

On the basis of the distinguishing standards based on the difference in the formations, the cross section image in FIG. 3 is subject to the image analysis to obtain the visualized image illustrated in FIG. 8 in which the four types of the cells in the hair (cuticle cell 51, ortho cell 52a, para cell 52b, medulla cell 54) were colored separately with black, dark gray, light gray, and white, respectively. Note that, in FIG. 8, the area other than the hair is illustrated in a lattice pattern. Further, FIG. 8 has the scale same as that of FIG. 3.

From FIG. 8, it can be known that, in addition to the cuticle cell 51 with black and the medulla cell 54 with white, the distribution states of the para cell 52b with light gray and the ortho cell 52a with dark gray are clearly visualized in the cross section of the hair.

In this visualization, the para cell 52b having the light gray is distributed in the left upper portion in a slightly deflected manner in the cross section of the hair in FIG. 8, and the ortho cell 52a having the dark gray is distributed in the right lower portion in a deflected manner in the cross section of the hair.

In other words, with the hair used in this example, it can be known that the para cell 52b and the ortho cell 52a are unevenly distributed in the cross-sectional image as illustrated in FIG. 8.

[Quantification of Abundance Ratio of Cells]

On the basis of the visualized image in FIG. 8, areas occupied by the four types of the cells in the cross section of the hair and an area of the cross section of the hair (total cross-sectional area) were obtained through the image analysis. The results thereof will be shown below.

Area occupied by cuticle cell: 491 μm²
Area occupied by ortho cell: 984 μm²
Area occupied by para cell: 1681 μm²
Area occupied by medulla cell: 47 μm²
Cross-sectional area of hair: 3202 μm²

Further, the ratios of the areas occupied by the respective cells were obtained. The results thereof will be shown below.

Ratio of area occupied by cuticle cell: 15.3%
Ratio of area occupied by ortho cell: 30.7%
Ratio of area occupied by para cell: 52.5%
Ratio of area occupied by medulla cell: 1.5%

Next, the ratios of the areas of the para cell 52b and the ortho cell 52a relative to the total area occupied by the two types of the cortex cells (ortho cell 52a and para cell 52b) were obtained. The results thereof will be shown below.

Ratio of area occupied by ortho cell: 36.9%
Ratio of area occupied by para cell: 63.1%

[Quantification of Positions of Cells]

On the basis of the visualized image in FIG. 8, the positions of the centroids of the para cell 52b and the ortho cell 52a in the cross section of the hair according to this example were obtained through the image analysis to calculate the distance between the centroids of the para cell 52b and the ortho cell 52a. The distance between the centroids of the para cell 52b and the ortho cell 52a was 8.5 μm.

Example 2

Straight Hair

In this example, the target hair is changed, and image analysis was performed in a similar method to Example 1 to obtain the distance between centroids of the para cell 52b and the ortho cell 52a.

[Acquisition of Image Information]

In this example, as the target hair, a scalp hair of Caucasian female B in her thirties was sampled from the root of the hair in the vicinity of the scalp, the sampled scalp hair being not subjected to any chemical hair treatment such as perming, bleaching and hair coloring.

The prepared hair sample was cleaned in a similar manner to Example 1, and then, dried. The dried hair sample was measured the curl radius, and it was found that the curl radius thereof was 5.0 cm.

From this hair sample, the cross section of the hair double-stained with osmic acid and uranyl acetate in a similar manner to Example 1 was obtained.

Figure 9:
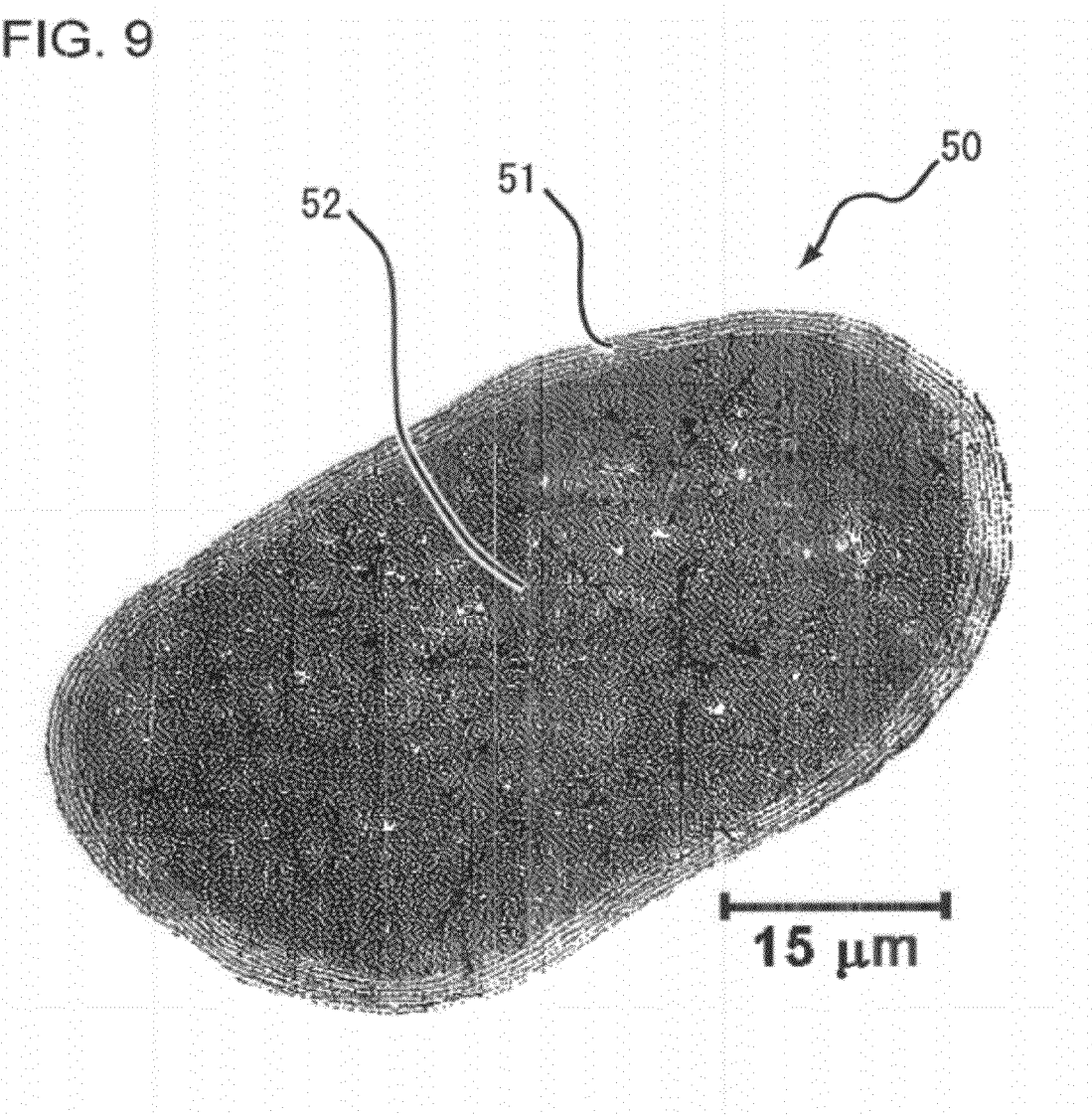
FIG. 9 is an entire image of a cross section of a hair of Example 2.

FIG. 9 illustrates a cross-sectional image of the hair obtained by observing the cross section of the double-colored hair with the transmission electron microscope.

[Visualization of Distribution of Cells]

Figure 10:
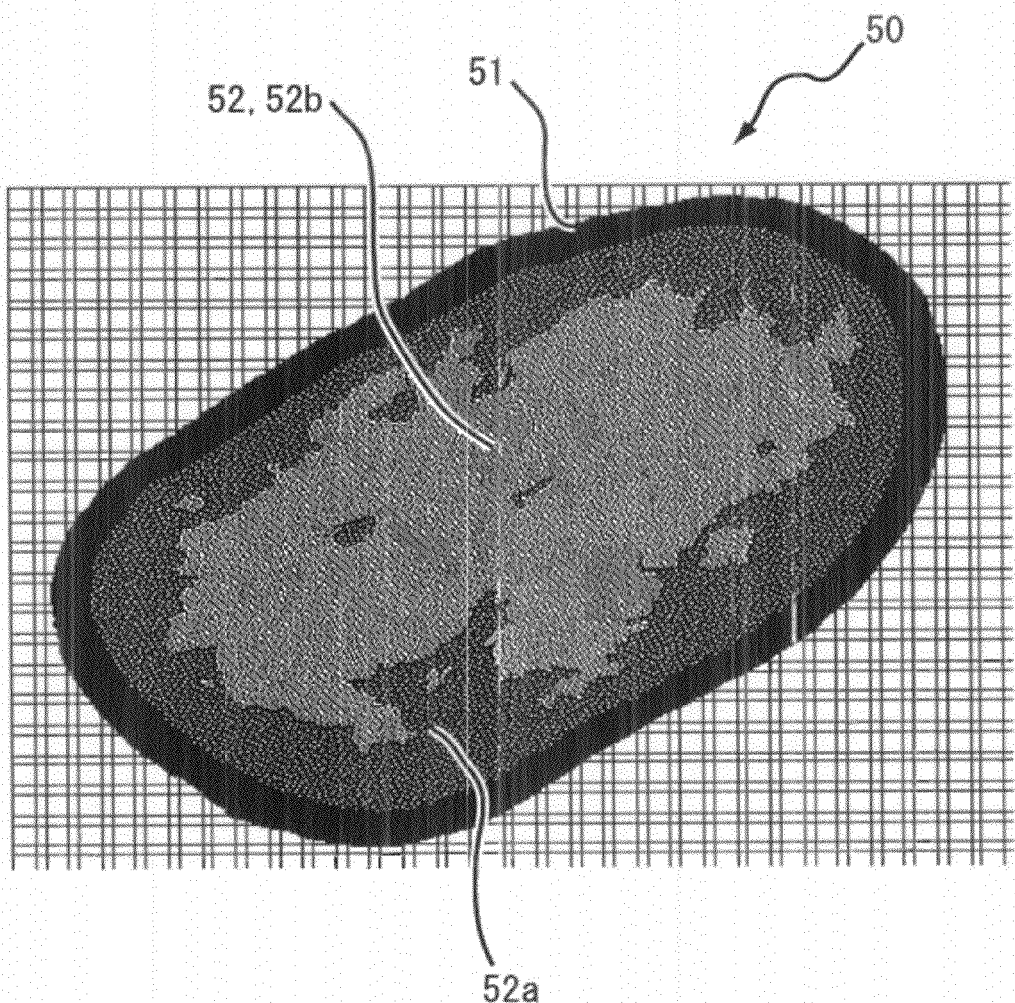
FIG. 10 is a visualized image of Example 2.

In a manner similar to Example 1, the cross-sectional image of FIG. 9 was subjected to the image analysis to obtain the visualized image illustrated in FIG. 10 in which the four types of cells in the hair (cuticle cell 51, ortho cell 52a, para cell 52b, medulla cell 54) were colored separately with black, dark gray, light gray, and white, respectively.

It should be noted that, in FIG. 10, the area other than the hair is illustrated in a lattice pattern. Further, FIG. 10 has the scale same as that of FIG. 9.

In this hair, the white medulla cell 54 does not exist. From FIG. 10, it was found that, in addition to the black cuticle cell 51, the distribution states of the para cell 52b with light gray and the ortho cell 52a with dark gray were clearly visualized in the cross section of the hair. It is visualized that the para cell 52b with light gray is distributed at the central portion in the cross section of the hair in FIG. 10, and the ortho cell 52a with dark gray is distributed around the central portion.

[Quantification of Abundance Ratio of Cells]

On the basis of the visualized image in FIG. 10, areas occupied by the four types of the cells in the cross section of the hair and an area of the cross section of the hair were obtained through the image analysis. The results thereof will be shown below.

Area occupied by cuticle cell: 633 $\mu m^2$
Area occupied by ortho cell: 1184 $\mu m^2$
Area occupied by para cell: 1376 $\mu m^2$
Area occupied by medulla cell: 0 $\mu m^2$
Cross-sectional area of hair: 3193 $\mu m^2$ Further, the ratios of the areas of the respective cells were obtained. The results thereof will be shown below.

Ratio of area occupied by cuticle cell: 19.8%
Ratio of area occupied by ortho cell: 37.1%
Ratio of area occupied by para cell: 43.1%
Ratio of area occupied by medulla cell: 0.0%

Next, the ratios of the areas of the para cell 52b and the ortho cell 52a relative to the total area occupied by the two types of the cortex cells (ortho cell 52a and para cell 52b) were obtained. The results thereof will be shown below.

Ratio of area occupied by ortho cell: 46.2%
Ratio of area occupied by para cell: 53.8%

[Quantification of Positions of Cells]

On the basis of the visualized image in FIG. 10, the positions of the centroids of the para cell 52b and the ortho cell 52a in the cross section of the hair according to this example were obtained through the image analysis to calculate the distance between the centroids of the para cell 52b and the ortho cell 52a. The distance between the centroids of the para cell 52b and the ortho cell 52a was 2.1 $\mu m$.

The hair of Example 2 was a substantially straight hair having a curl radius of 5.0 cm. The para cell 52b and the ortho cell 52a were distributed in the cross section of the hair in an isotropic manner as illustrated in FIG. 10. Further, the distance between the centroids of the two types of the cortex cells 52 was 2.1 $\mu m$, and was smaller than that of Example 1 (curl radius: 0.9 cm, and distance between centroids: 8.5 $\mu m$).

Further, with the comparison between Example 1 and Example 2, it was found that the curl radius of the hair correlates with the distance between centroids of the two types of the cortex cells 52.

Example 3

Straight Hair

This example relates to a method of acquiring the numerical information describing the shape and the property of the hair by acquiring the cross-sectional image of the hair reflecting the distribution states of the cells by staining the cross section of the hair with two types of staining agents and analyzing the acquired image.

[Acquisition of Image Information]

The cross section of the hair was stained with yellow No. 202 having a yellow-green fluorescence and sulforhodamine 101 having fluorescence of orange. Of the two types of the cortex cells 52, the para cell 52b was stained into yellow-green, and the ortho cell 52a was stained into orange. Then, the image information reflecting the distribution states of the cells in the stained hair was obtained.

As the target hair, a scalp hair of Japanese female C in her thirties was sampled from the root of the hair in the vicinity of the scalp, the sampled scalp hair being not subjected to any chemical hair treatment such as perming, bleaching and hair coloring.

The prepared hair sample was cleaned in a similar manner to Example 1, and then, dried. The dried hair sample was measured the curl radius, and it was found that the curl radius thereof was 3.9 cm.

After embedded in the epoxy resin, this hair sample was cut out with a microtome to obtain the cross section thereof having a thickness of 1.5 $\mu m$, and was mounted on a slide glass.

The cross section of the hair fixed on the slide glass was sequentially stained with yellow No. 202 (Acid Yellow 73) and sulforhodamine 101 in accordance with the method described in Non-patent Document 4 described above. More specifically, the cross section of the hair was immersed into a solution of yellow No. 202 (Acid Yellow 73) of 0.002 mass % for 18 hours, rinsed with ion-exchange water, and dried. Then, the cross section of the hair was immersed into a solution of sulforhodamine 101 of 0.0005 mass %, rinsed with ion-exchange water, and dried, thereby obtaining the cross section of the hair stained with two types of staining agents.

Figure 11:
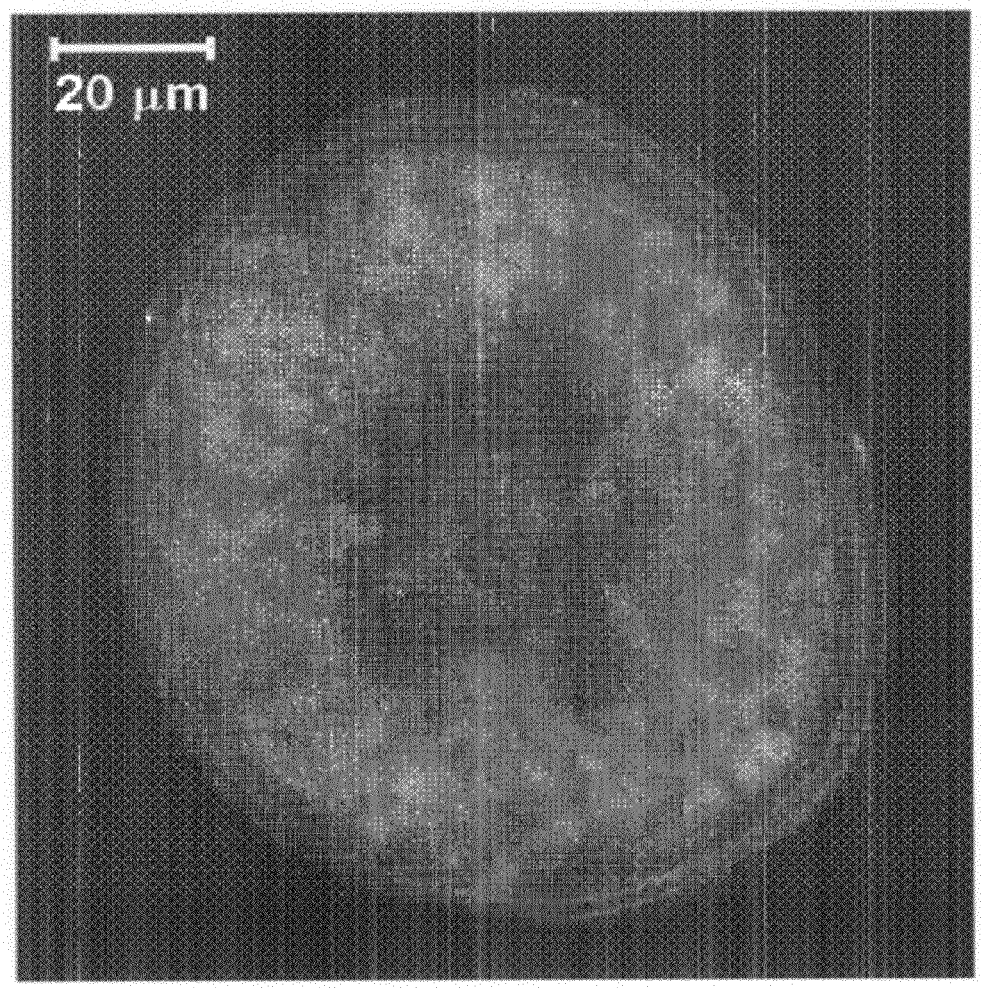
FIG. 11 is an entire image of a cross section of a hair of Example 3.

FIG. 11 illustrates the cross-sectional image of the hair obtained by observing the cross section of the hair stained with the two types of the fluorescent dyes through a fluorescence microscope. FIG. 11 is obtained by subjecting the cross-sectional image of the hair acquired as a color image to a white-black binary conversion process.

Figure 12:
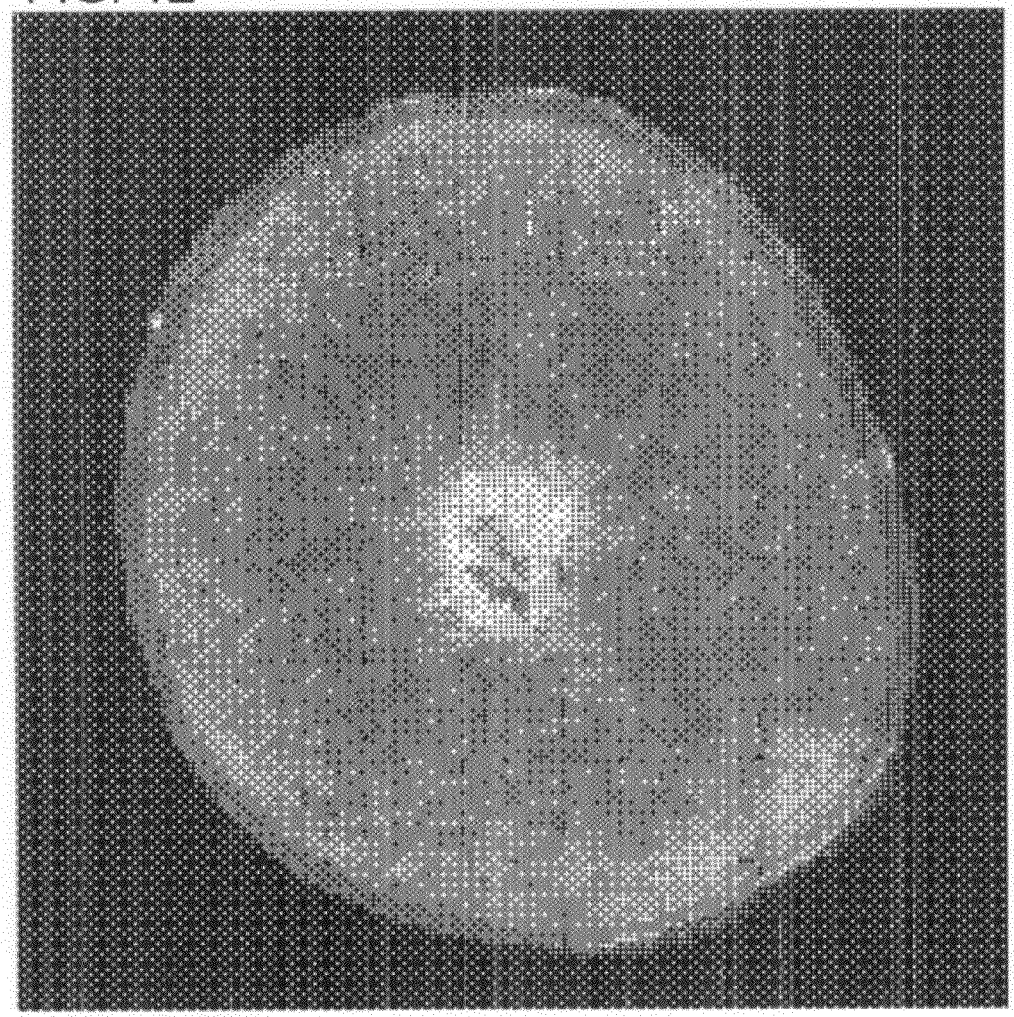
FIG. 12 is an image of an R value of FIG. 11.
Figure 13:
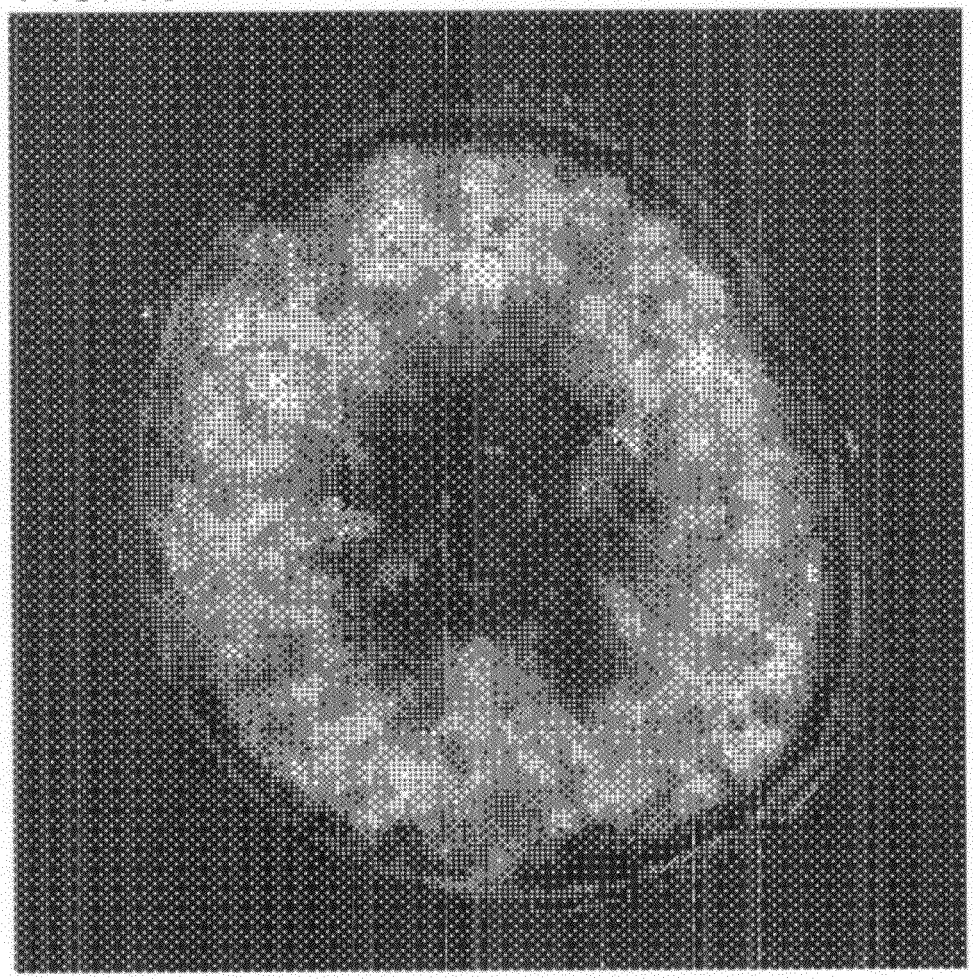
FIG. 13 is an image of a G value of FIG. 11.
Figure 14:
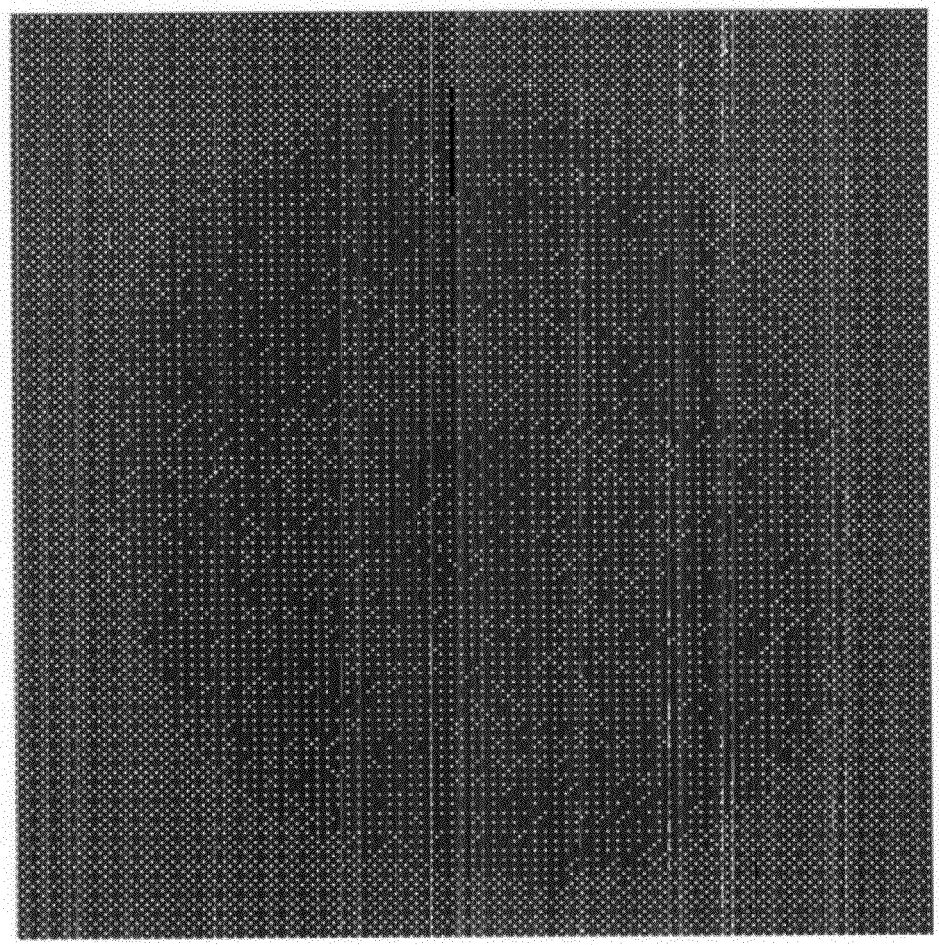
FIG. 14 is an image of a B value of FIG. 11.

FIG. 12 through FIG. 14 are diagrams obtained by imaging RGB values of the acquired color image. More specifically, FIG. 12 is an image of an R value, FIG. 13 is an image of a G value, and FIG. 14 is an image of a B value.

In this example, the structure of the cross section of the hair illustrated in FIG. 11 can be clearly recognized with the image of the G value (FIG. 13). More specifically, the portion stained with the fluorescent dye (yellow No. 202) having a yellow-green color is shown in a relatively light color in FIG. 13. Note that the portion stained with the fluorescent dye (sulforhodamine 101) having the orange color is shown in a relatively light color in FIG. 12. In other words, from FIG. 11 to FIG. 14, especially, from FIG. 12 and FIG. 13, it can be known that the cross section of the hair is stained separately with two colors of yellow-green and orange.

[Visualization of Distribution of Cells]

In this example, the portion stained with the fluorescent dye (yellow No. 202) having yellow-green color is defined as the para cell 52b.

The portion stained with the fluorescent dye (sulforhodamine 101) having the orange color is the ortho cell 52a, the cuticle cell 51, and the medulla cell 54. The three types of the cells stained with the fluorescent dye having orange color are located at different positions and have different formations, and hence, can be distinguished from each other. For example, the cuticle cell 51 is located in the vicinity of the surface of the hair in a layered manner, and hence, on the basis of the difference in the formations, can be distinguished from the adjacent ortho cell 52a. Further, the medullar cell 54 is located at the central portion of the hair and has a porous structure, and hence, on the basis of the difference in the formations, can be distinguished from the ortho cell 52a.

Figure 15:
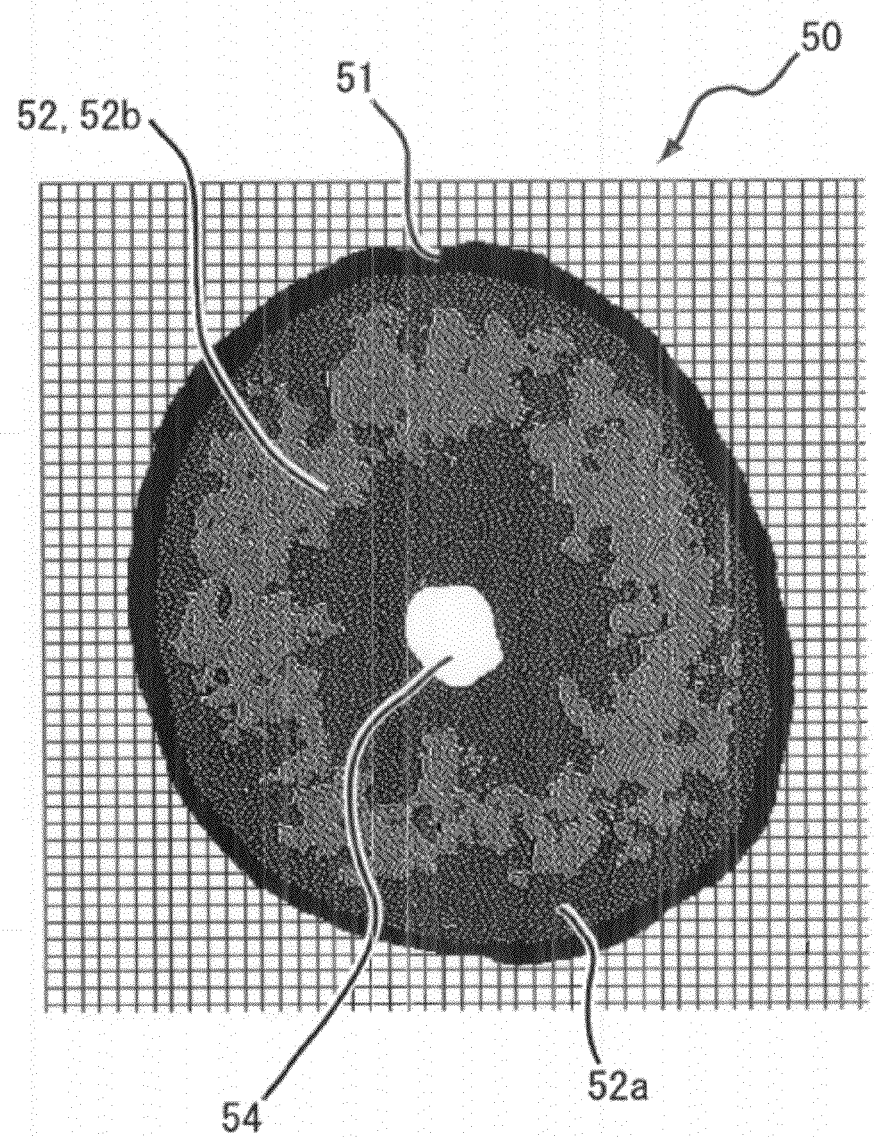
FIG. 15 is a visualized image of Example 3.

The image information in FIG. 11 was image analyzed in accordance with the above-described distinguishing standards based on the difference in the stained colors and formations. FIG. 15 is a visualized image obtained by applying black, dark gray, light gray, and white to the four types of cells in the hair (cuticle cell 51, ortho cell 52a, para cell 52b, medulla cell 54), respectively. Note that, in FIG. 15, the area other than the hair is illustrated in a lattice pattern.

Further, the visualized image illustrated in FIG. 15 may be created on the basis of FIG. 13. In this case, it is preferable that the portion having the G value more than or equal to a threshold value is judged as a yellow-green color (para cell 52b), and the portion having the G value less than or equal to the threshold value is judged as an orange color (ortho cell 52a, cuticle cell 51 or medulla cell 54). The portions having the orange color can be distinguished among the ortho cell 52a, the cuticle cell 51 and medulla cell 54 on the basis of the difference in the formations.

[Quantification of Abundance Ratio of Cells]

On the basis of the visualized image in FIG. 15, areas occupied by the four types of the cells in the cross section of the hair and an area of the cross section of the hair were obtained through the image analysis. The results thereof will be shown below.

Area occupied by cuticle cell: 1132 $\mu m^2$
Area occupied by ortho cell: 4412 $\mu m^2$
Area occupied by para cell: 3022 $\mu m^2$
Area occupied by medulla cell: 175 $\mu m^2$
Cross-sectional area of hair: 8741 $\mu m^2$ Further, the ratios of the areas of the respective cells were obtained. The results thereof will be shown below.

Ratio of area occupied by cuticle cell: 12.9%
Ratio of area occupied by ortho cell: 50.5%
Ratio of area occupied by para cell: 34.6%
Ratio of area occupied by medulla cell: 2.0%

Next, the ratios of the areas of the para cell 52b and the ortho cell 52a relative to the total area occupied by the two types of the cortex cells (ortho cell 52a and para cell 52b) were obtained. The results thereof will be shown below.

Ratio of area occupied by ortho cell: 59.3%
Ratio of area occupied by para cell: 40.7%

[Quantification of Positions of Cells]

On the basis of the visualized image in FIG. 15, the positions of the centroids of the para cell 52b and the ortho cell 52a in the cross section of the hair according to this example were obtained through the image analysis to calculate the distance between the centroids of the para cell 52b and the ortho cell 52a. The distance between the centroids of the para cell 52b and the ortho cell 52a was 4.7 μm.

The hair of Example 3 had a curl radius of 3.9 cm, and was a straight hair with a slightly curly shape. In the cross section of the hair, the para cell 52b and the ortho cell 52a were distributed in a slightly deflected manner as illustrated in FIG. 15. Further, the distance between the centroids of the two types of the cortex cells 52 was 4.7 μm.

By comparing the results of Examples 1 to 3, it is found that the order of the curl radii matches with the order of the distances between centroids of the two types of the cortex cells 52. Therefore, it becomes further clear that the curl radius of the hair correlates with the distance between centroids of the two types of the cortex cells 52.

Example 4

Curly Hair

In this example, the target hair is changed, and image analysis was performed in a similar method to Example 3, thereby obtaining the distance between centroids of the para cell 52b and the ortho cell 52a.

[Acquisition of Image Information]

In this example, as the target hair, a scalp hair of Japanese female D in her twenties was sampled from the root of the hair in the vicinity of the scalp, the sampled scalp hair being not subjected to any chemical hair treatment such as perming, bleaching and hair coloring.

The prepared hair sample was cleaned in a similar manner to Example 3, and then, dried. The dried hair sample was measured the curl radius, and it was found that the curl radius thereof was 0.55 cm.

After embedded in the epoxy resin in a similar manner to Example 3, this hair sample was cut out with a microtome to obtain the cross section thereof having a thickness of 1.5 μm, thereby obtaining the cross section of the hair stained with yellow No. 202 (Acid Yellow 73) and sulforhodamine 101.

Figure 16:
FIG. 16 is an entire image of a cross section of a hair of Example 4.

FIG. 16 illustrates the cross-sectional image of the hair obtained by observing the cross section of the hair stained with the two types of the fluorescent dyes through a fluorescence microscope. FIG. 16 is obtained by subjecting the cross-sectional image of the hair acquired as a color image to a white-black binary conversion process.

Figure 17:
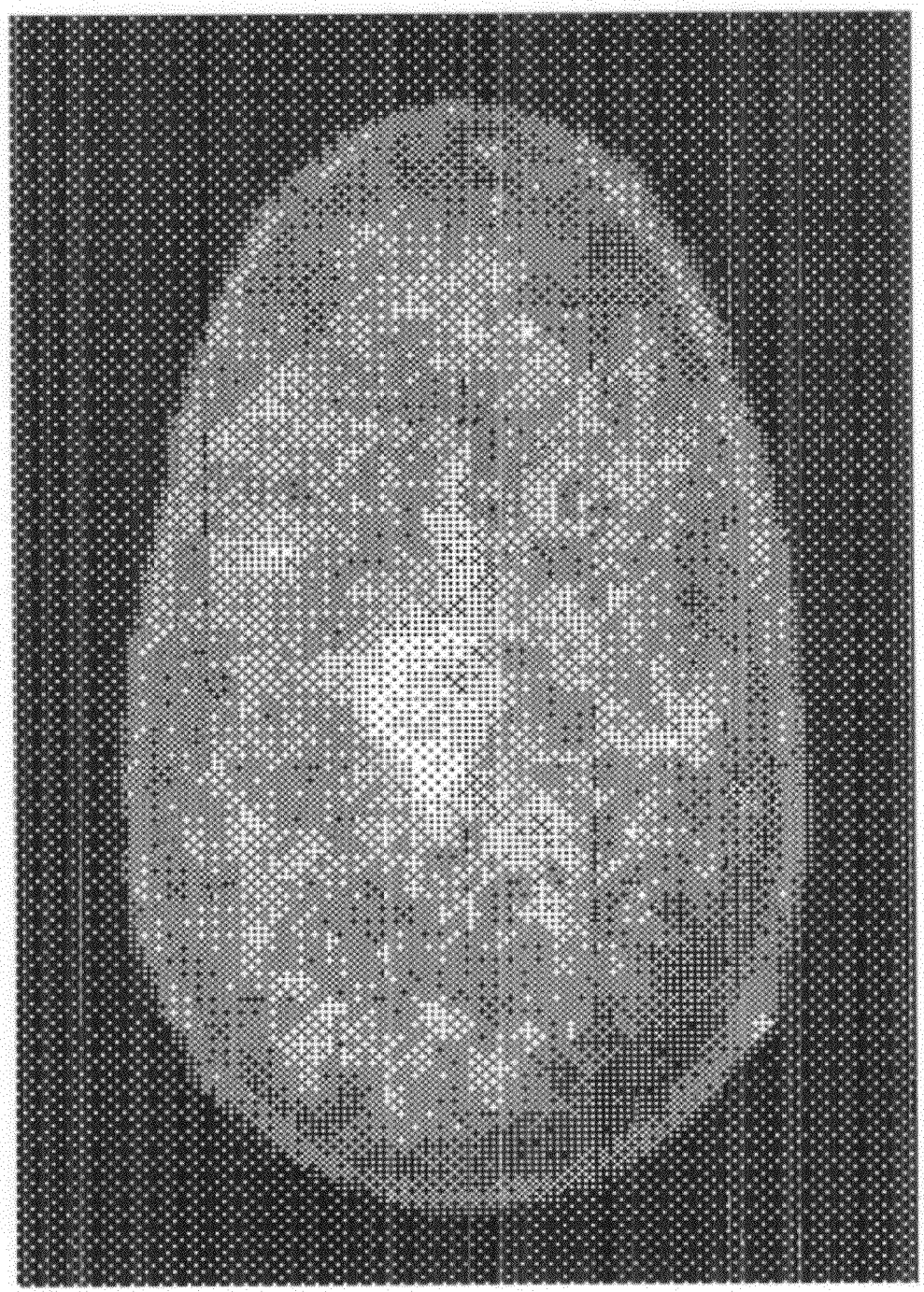
FIG. 17 is an image of an R value of FIG. 16.
Figure 18:
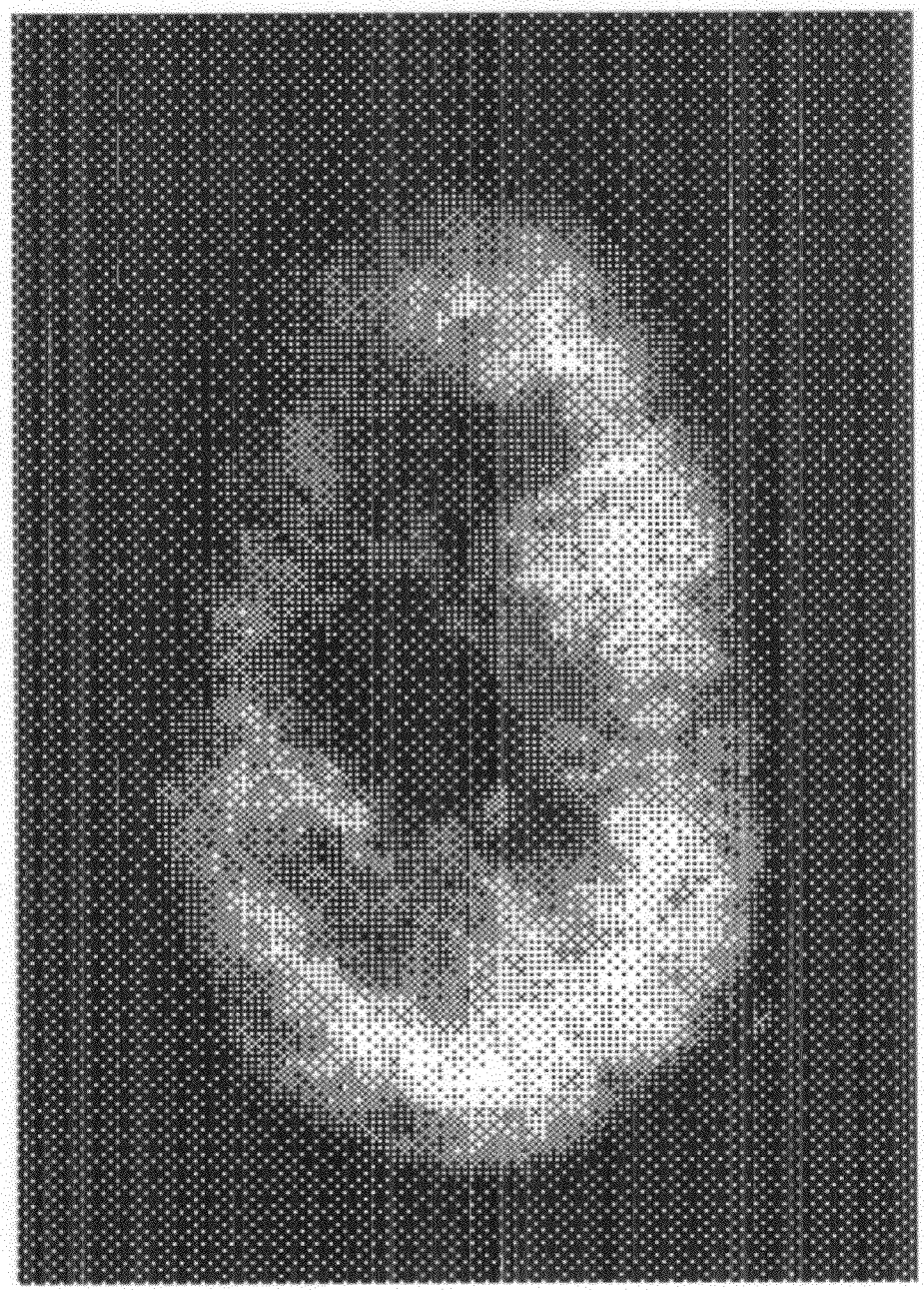
FIG. 18 is an image of a G value of FIG. 16.
Figure 19:
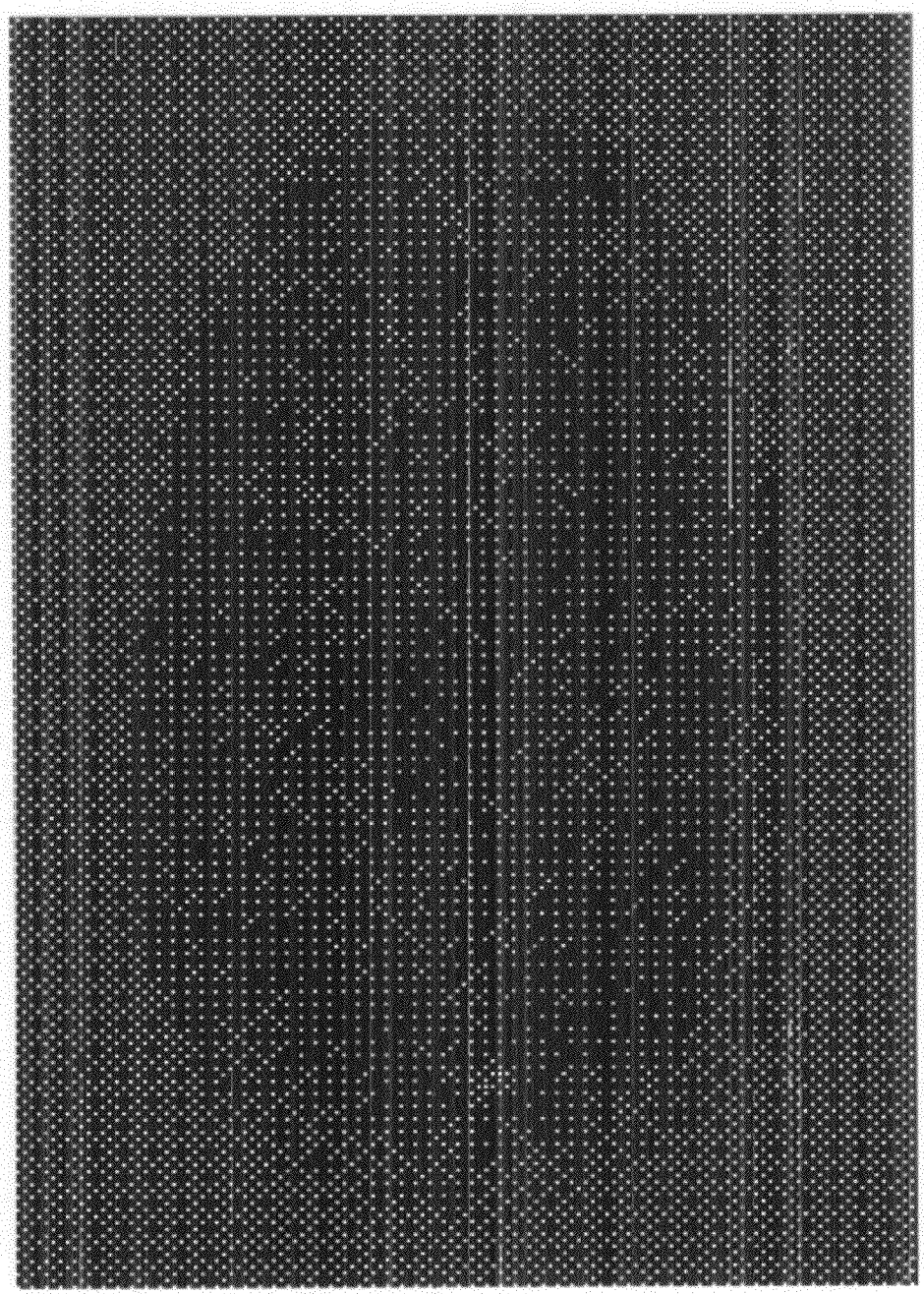
FIG. 19 is an image of a B value of FIG. 16.

FIG. 17 through FIG. 19 are diagrams obtained by imaging RGB values of the acquired color image. More specifically, FIG. 17 is an image based on an R value, FIG. 18 is an image based on a G value, and FIG. 19 is an image based on a B value.

Similar to Example 3, in this example, the structure of the cross section of the hair illustrated in FIG. 16 can be clearly recognized especially with the image of the G value (FIG. 18).

[Visualization of Distribution of Cells]

Figure 20:
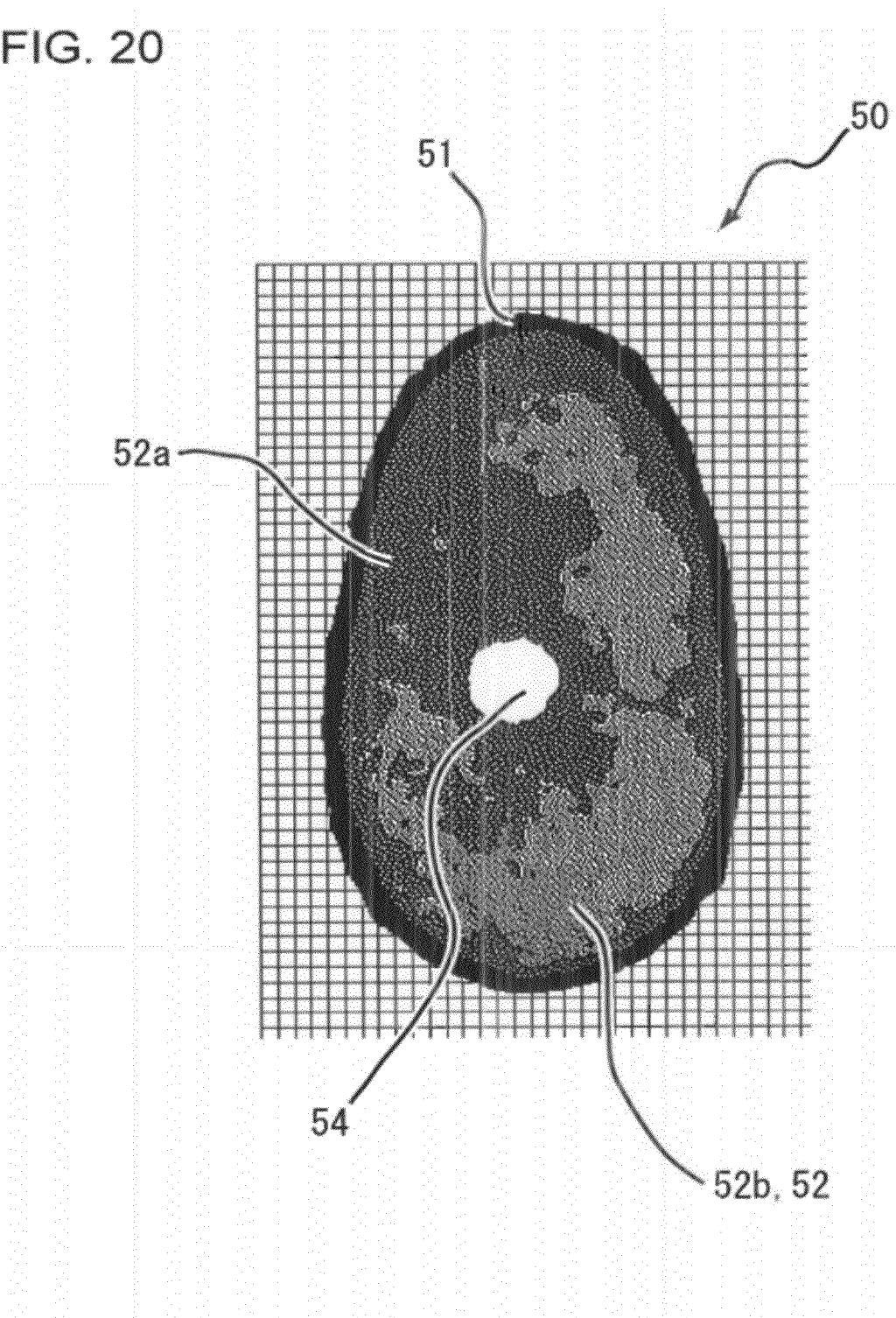
FIG. 20 is a visualized image of Example 4.

Similar to Example 3, the image information in FIG. 16 was subjected to the image analysis to obtain the visualized image illustrated in FIG. 20 in which the four types of cells in the hair (cuticle cell 51, ortho cell 52a, para cell 52b, medulla cell 54) were colored separately with black, dark gray, light gray, and white, respectively.

It should be noted that, in FIG. 20, the area other than the hair is illustrated in a lattice pattern.

[Quantification of Abundance Ratio of Cells]

On the basis of the visualized image in FIG. 20, areas occupied by the four types of the cells in the cross section of the hair and an area of the cross section of the hair were obtained through the image analysis. The results thereof will be shown below.

Area occupied by cuticle cell: 847 μm²
Area occupied by ortho cell: 3181 μm²
Area occupied by para cell: 1959 μm²
Area occupied by medulla cell: 159 μm²
Cross-sectional area of hair: 6145 μm²

Further, the ratios of the areas occupied by the respective cells were obtained. The results thereof will be shown below.

Ratio of area occupied by cuticle cell: 13.8%
Ratio of area occupied by ortho cell: 51.8%
Ratio of area occupied by para cell: 31.9%
Ratio of area occupied by medulla cell: 2.6%

Next, the ratios of the areas of the para cell 52b and the ortho cell 52a relative to the total area occupied by the two types of the cortex cells (ortho cell 52a and para cell 52b) were obtained. The results thereof will be shown below.

Ratio of area occupied by ortho cell: 61.9%
Ratio of area occupied by para cell: 38.1%

[Quantification of Positions of Cells]

On the basis of the visualized image in FIG. 20, the positions of the centroids of the para cell 52b and the ortho cell 52a in the cross section of the hair according to this example were obtained through the image analysis to calculate the distance between the centroids of the para cell 52b and the ortho cell 52a. The distance between the centroids of the para cell 52b and the ortho cell 52a was 20.4 μm.

The hair of Example 4 had a curl radius of 0.55 cm, and was a strongly curly hair. In the cross section of the hair, the para cell 52b and the ortho cell 52a were distributed in a largely deflected manner as illustrated in FIG. 20. Further, the distance between the centroids of the two types of the cortex cells 52 was 20.4 μm.

By comparing the results of Examples 1 to 4, it is found that the order of the curl radii matches with the order of the distances between centroids of the two types of the cortex cells 52. Therefore, it becomes further clear that the curl radius of the hair correlates with the distance between centroids of the two types of the cortex cells 52.

Example 5

Comparison 1 with Reference Hair

For 41 reference hairs having different curl radii, the step of acquiring the image information, the step of visualizing the distribution of the cells, and the step of quantifying the positions of the cells were performed similarly to the case with the TEM observation method in Example 1.

Figure 21A:
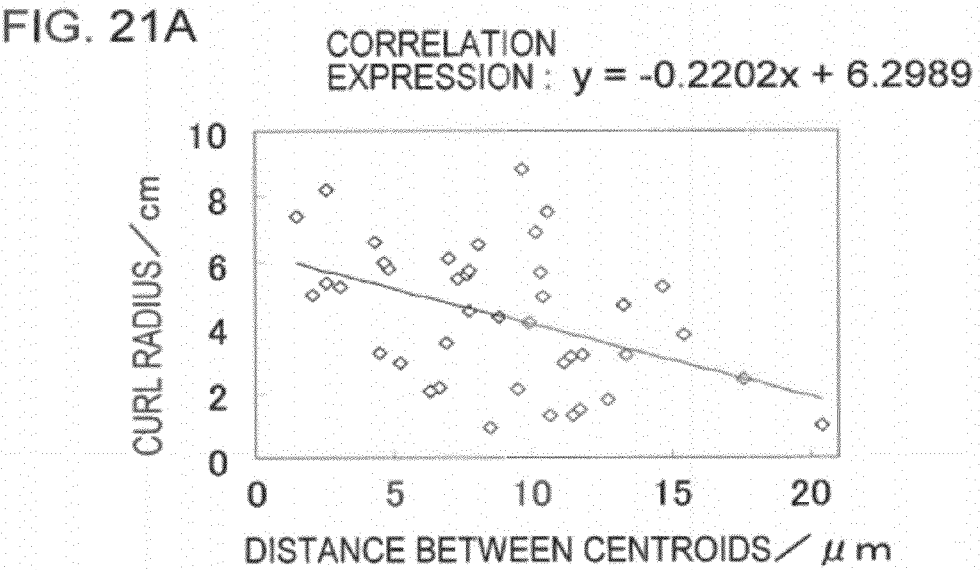
FIG. 21A is a scatter diagram illustrating a relationship between a curl radius and a distance between centroids with regard to reference hairs and calibration curve.

FIG. 21A is a scatter diagram illustrating relationships between the curl radii of the reference hairs obtained as described above and the distances between the centroids of the para cell 52b and the ortho cell 52a.

On the basis of FIG. 21A, a relational expression between the curl radius and the distance between centroids is obtained through a least-square method, thereby obtaining the following Expression (1). In FIG. 21A, a graph of the following Expression (1) is illustrated as data of a calibration line of the curl radius and the distance between the centroids.

$$\text{Curl radius/cm} = -0.22 \times \text{distance between centroids/μm} + 6.3 \quad \text{Expression (1)}$$

On the basis of Expression (1), the curl radius of the scalp hair (distance between centroids=4.7 μm) of Japanese female A in her twenties is calculated, thereby obtaining the curl radius of 5.4 cm. This predicted curl radius well coincides with the actually measured curl radius (6 cm).

Example 6

Comparison 2 with Reference Hair

For the 41 reference hairs used in Example 5, the abundance ratio of the para cell 52b in the cortex cell 52 and the bending elastic modulus were obtained.

Figure 21B:
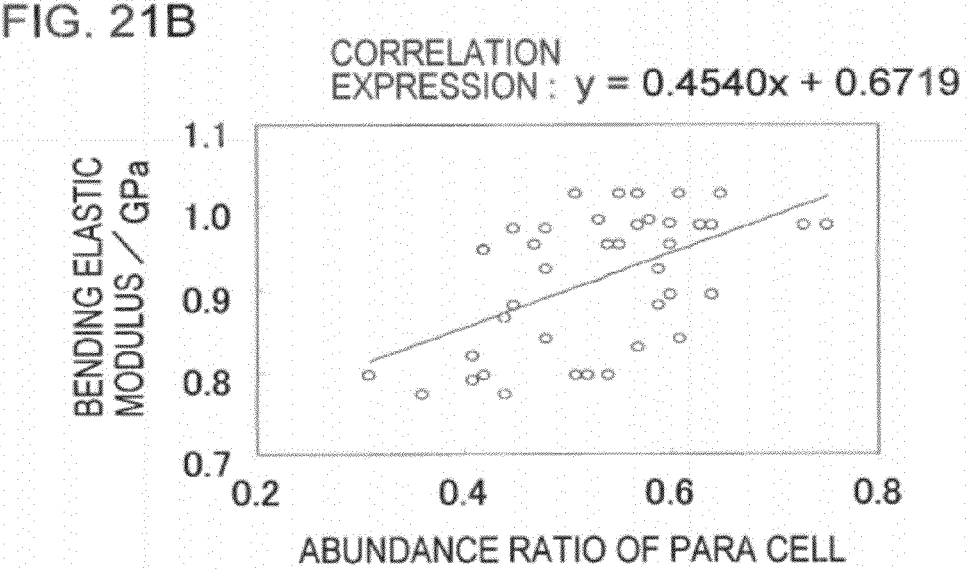
FIG. 21B is a scatter diagram illustrating a relationship between a bending elastic modulus and an abundance ratio of a para cell (described in detail later) of reference hairs, and calibration curve.

FIG. 21B is a scatter diagram illustrating relationships between the bending elastic moduli and the abundance ratios of the para cell 52b obtained as described above.

On the basis of FIG. 21B, a relational expression between the bending elastic moduli and the abundance ratios of the para cell 52b is calculated through a least-square method, thereby obtaining the following Expression (2). In FIG. 21B, a graph of the following Expression (2) is illustrated as data of a calibration line of the bending elastic modulus and the abundance ratio of the para cell 52b.

$$\text{Bending elastic modulus/GPa} = 0.45 \times \text{abundance ratio of para cell} + 0.67 \quad \text{Expression (2)}$$

With Expression (1) and Expression (2), it is possible to evaluate the curl radius and the bending elastic modulus of the target hair, only by obtaining the distance between centroids of the ortho cell 52a and the para cell 52b of the target hair and the abundance ratio of the para cell 52b relative to the cortex cell 52.

According to the data acquiring method and the data acquiring apparatus 100 of this embodiment, it is possible to obtain quantitative indices for describing various characteristics of the hair sample from the cross-sectional image of the hair.

The present application claims priority based on Japanese Patent Application No. 2009-181066 filed in Japan on Aug. 3, 2009, all of which disclosure is incorporated herein by reference.

The invention claimed is:

1. A method for acquiring hair characteristic data, comprising:
    acquiring a cross-sectional image of a human hair, in which a plurality of types of fibrous tissues constituting cortex cells present in the human hair are visualized in such a manner as to be distinguishable from each other;
    acquiring, from the cross-sectional image, numerical information indicating a distribution state of the visualized plurality of types of fibrous tissues, the numerical information including a distance between a centroid of a distribution of a first intermediate filament tissue in the cross-sectional image and a centroid of a distribution of a second intermediate filament tissue in the cross-sectional image;
    acquiring calibration data indicating a relationship between the numerical information and a hair characteristic using human hair samples as reference hairs; and
    evaluating a hair characteristic of the human hair on the basis of the numerical information of the human hair and the calibration data indicating the relationship between the numerical information and the hair characteristic using the human hair samples as the reference hairs.

2. The method for acquiring hair characteristic data according to claim 1, wherein said evaluating the hair characteristic comprises calculating an index value indicating a degree of curl of the human hair.

3. The method for acquiring hair characteristic data according to claim 1, wherein said acquiring the numerical information includes acquiring an abundance ratio of the fibrous tissue relative to the cortex cells as the numerical information.

4. The method for acquiring hair characteristic data according to claim 3, wherein said evaluating the hair characteristic comprises calculating an index value indicating a bending rigidity of the human hair.

5. The method for acquiring hair characteristic data according to claim 1, wherein said acquiring the numerical information further acquires numerical information indicating a distribution state of at least one of a cuticle cell and a medulla cell present in the human hair.

6. The method for acquiring hair characteristic data according to claim 1, further comprising staining a cross section of the human hair with a staining agent to visualize the plurality of types of the fibrous tissues so as to be distinguishable.

7. The method for acquiring hair characteristic data according to claim 1, further comprising:
measuring an infrared absorption spectrum or Raman spectrum of a cross section of the human hair, or scanning the cross section of the human hair with a microprobe microscope, or observing the human hair with a transmission electron microscope to visualize the plurality of types of the fibrous tissues so as to be distinguishable in the cross-sectional image.

8. An apparatus for acquiring hair characteristic data, comprising:
image processing circuitry configured to:
acquire a cross-sectional image of a human hair, in which a plurality of types of fibrous tissues constituting cortex cells present in the human hair are visualized in such a manner as to be distinguishable from each other;
acquire, from the cross-sectional image, numerical information indicating a distribution state of the visualized plurality of types of fibrous tissues, the numerical information including a distance between a centroid of a distribution of a first intermediate filament tissue in the cross-sectional image and a centroid of a distribution of a second intermediate filament tissue in the cross-sectional image;
acquire calibration data indicating a relationship between the numerical information and a hair characteristic using human hair samples as reference hairs; and
evaluate a hair characteristic of the human hair on the basis of the numerical information of the human hair and the calibration data indicating the relationship between the numerical information and the hair characteristic using the human hair samples as the reference hairs.

9. The apparatus for acquiring hair characteristic data according to claim 8, wherein said image processing circuitry is configured to calculate an index value indicating a degree of curl of the human hair.

10. The apparatus for acquiring hair characteristic data according to claim 8, wherein said image processing circuitry is configured to acquire an abundance ratio of the fibrous tissue relative to the cortex cells as the numerical information.

11. The apparatus for acquiring hair characteristic data according to claim 10, wherein said image processing circuitry is configured to calculate an index value indicating a bending rigidity of the human hair.

12. The apparatus for acquiring hair characteristic data according to claim 8, wherein said image processing circuitry is configured to acquire numerical information indicating a distribution state of at least one of a cuticle cell and a medulla cell present in the human hair.

13. The apparatus for acquiring hair characteristic data according to claim 8, wherein said one of the fibrous tissues constitutes ortho cells and said another one of the fibrous tissues constitutes para cells.

14. The method for acquiring hair characteristic data according to claim 1, wherein said first intermediate filament tissue constitutes ortho cells and said second intermediate filament tissue constitutes para cells.

* * * * *